United States Patent
Rocchi et al.

(10) Patent No.: US 10,815,207 B2
(45) Date of Patent: Oct. 27, 2020

(54) SUBSTITUTED HYDROPHOBIC BENZENE SULFONAMIDE THIAZOLE COMPOUNDS FOR USE IN TREATING CANCER

(71) Applicants: INSERM (Institut National de la Sante et de la Recherche Medicale), Paris (FR); Universite Nice Sophia Antipolis, Nice (FR); Centre National de la Recherche Scientifique (CNRS), Paris (FR)

(72) Inventors: Stephane Rocchi, Nice (FR); Rachid Benhida, Nice (FR); Robert Ballotti, Nice (FR); Magali Plaisant, Nice (FR); Cyril Ronco, Nice (FR); Antoine Millet, Nice (FR)

(73) Assignees: INSERM (Institut National de la Sante et de la Recherche Medicale), Paris (FR); Universite Nice Sophia Antipolis, Nice (FR); Centre National de la Recherche Scientifique (CNRS), Paris (FR)

(*) Notice: Subject to any disclaimer, the term of this patent is extended or adjusted under 35 U.S.C. 154(b) by 0 days.

(21) Appl. No.: 15/746,630

(22) PCT Filed: Jul. 22, 2016

(86) PCT No.: PCT/EP2016/067506
§ 371 (c)(1),
(2) Date: Jan. 22, 2018

(87) PCT Pub. No.: WO2017/017004
PCT Pub. Date: Feb. 2, 2017

(65) Prior Publication Data
US 2018/0215723 A1  Aug. 2, 2018

(30) Foreign Application Priority Data
Jul. 24, 2015 (EP) .................................... 15306213

(51) Int. Cl.
C07D 277/46 (2006.01)
A61K 31/426 (2006.01)
A61P 35/00 (2006.01)

(52) U.S. Cl.
CPC .......... C07D 277/46 (2013.01); A61K 31/426 (2013.01); A61P 35/00 (2018.01)

(58) Field of Classification Search
CPC .................................................. C07D 277/46
See application file for complete search history.

(56) References Cited

U.S. PATENT DOCUMENTS 9,567,310 B2* 2/2017 Rocchi ................ C07D 277/42
2010/0130486 A1 5/2010 Singh et al.

FOREIGN PATENT DOCUMENTS

| EP | 0 359 112 A2 | 3/1990 |
| EP | 1 452 530 A1 | 9/2004 |
| WO | 2007/070600 A2 | 6/2007 |

(Continued)

OTHER PUBLICATIONS

Wislicenus, J. "Adolph Strecker's Short Textbook of Organic Chemistry" 1881, Spottiswoode: London, pp. 38-39.*
Wagner "Synthesis of antiproteolytically active N-arylsulfonylated amidinophenylalanine amides." Pharmazie, 1981, 36(9), 597-603 (abstract only).*
Ferreira "The Importance of Cancer Cell Lines as in vitro Models in Cancer Methylome Analysis and Anticancer Drugs Testing" Chapter 6 in Oncogenomics and Cancer Proteomics—Novel Approaches in Biomarkers Discovery and Therapeutic Targets in Cancer Intech 2013 pp. 140-166.*
Simone, Oncology: Introduction, Cecil Textbook of Medicine, 20th Edition, 1996 vol. 1, pp. 1004-1010.*
Damia "Contemporary pre-clinical development of anticancer agents—What are the optimal preclinical models?" European Journal of Cancer 2009, 45, 2768-2781.*

(Continued)

*Primary Examiner* — David K O'Dell
(74) *Attorney, Agent, or Firm* — W&C IP

(57) ABSTRACT

The present invention relates to compound of general formula (I) $R_1$ is selected from H, aryl and alkyl, $R_2$ is selected from H, alkyl, aryl and CO—$R_6$; $R_3$ is selected from H, halogen, alkyl, alkenyl, alkynyl, aryl, $NHR_7$, $NR_7R_8$, $OR_7$ and $SR_7$; $R_4$ is selected from ($C_6$-$C_{12}$) alkyl, ($C_2$-$C_{12}$) alkenyl, ($C_2$-$C_{12}$) alkynyl and ($C_6$-$C_{10}$) aryl, $R_5$ represents H, $R_6$, aryl, OH, $OR_6$, O-aryl, SH, $SR_6$, S-aryl, CN, $NO_2$, $CF_3$, $COOR_6$, $SO_2NR_6R_7$, $CONR_6R_7$, $NH_2$, $NHR_6$, NH-aryl, $NR_6R_7$, $NHCOR_6$ or aminoacyl; $R_6$ is alkyl optionally substituted with halogen, OH, SH, $NH_2$, O-alkyl, S-alkyl, NH-alkyl or NH-di(alkyl); $R_7$ and $R_8$ identical or different are H or alkyl optionally substituted with halogen, OH, SH, $NH_2$, O-alkyl, S-alkyl, NH-alkyl or NH-di (alkyl), their pharmaceutically acceptable salts and/or isomers, tautomers, solvates or isotopic variations thereof. The compounds are useful for the treatment of cancers.

(I)

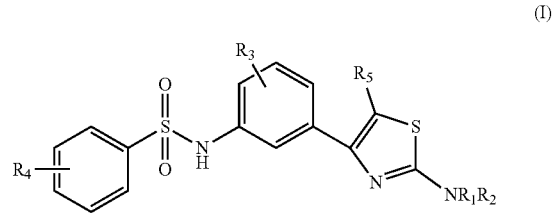

10 Claims, 6 Drawing Sheets

(56) References Cited

FOREIGN PATENT DOCUMENTS

Figure 1:
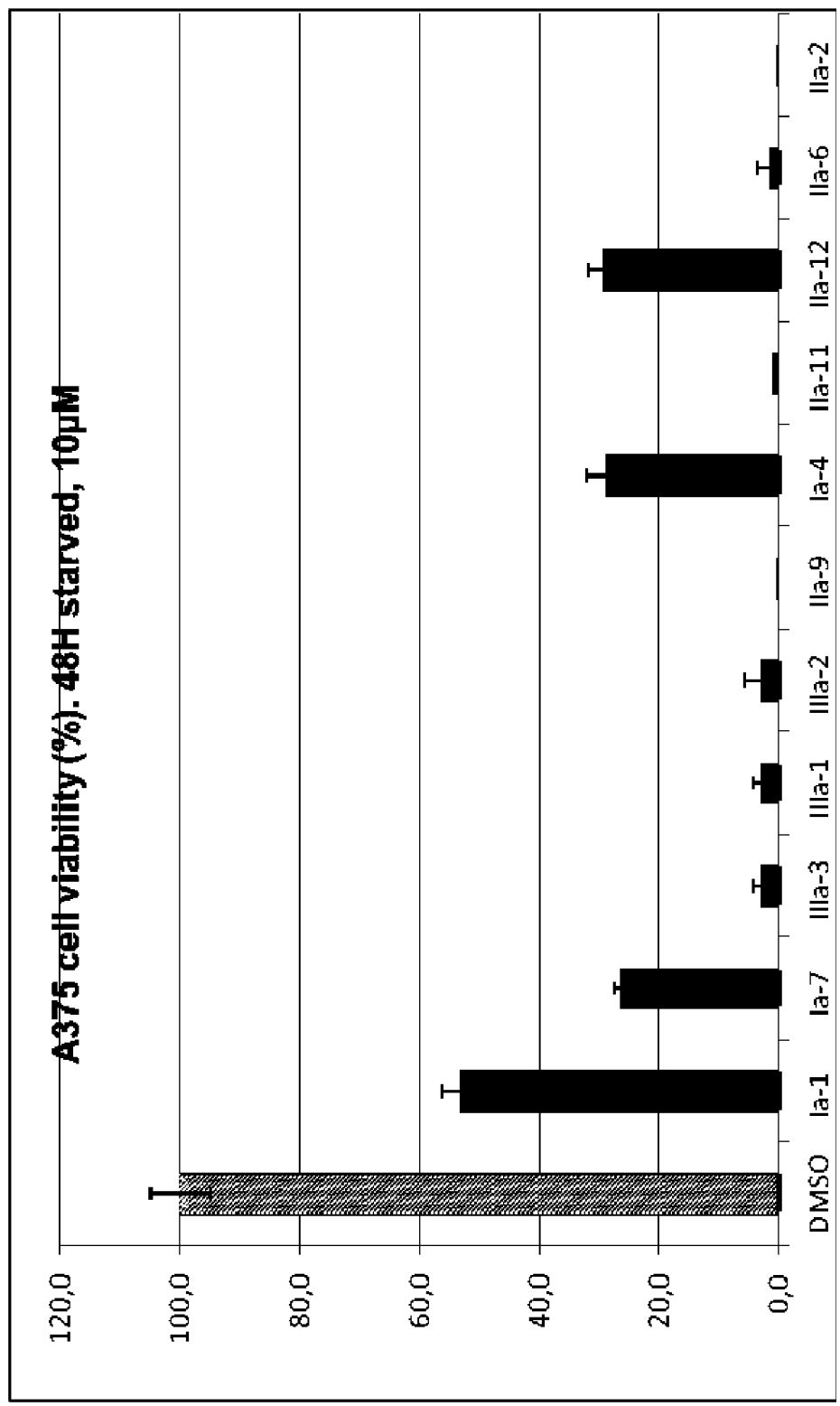

| WO | 2008/027912 A1 | 3/2008 |
|---|---|---|
| WO | 2009/146013 A1 | 12/2009 |
| WO | 2014/072486 A1 | 5/2014 |

OTHER PUBLICATIONS

Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Ledford "US cancer institute overhauls cell lines" Nature Feb. 25, 2016 vol. 530 p. 391.*
Johnson, et. al. "Relationships between drug activity in NCI preclinical in vitro and in vivo models and early clinical trials." British Journal of Cancer 2001, 84, 1424-1431.*
Jett Treatment of Small Cell Lung Cancer Diagnosis and Management of Lung Cancer, 3rd ed: American College of Chest Physicians Evidence-Based Clinical Practice Guidelines CHEST 2013; 143(5)(Suppl):e400S-e419S.*
Sanz-Garcia, "Current and advancing treatments for metastatic colorectal cancer" Expert Opinion on Biological Therapy, 16:1, 2016 , 93-110.*
Garson "Models of ovarian cancer—Are we there yet?" Molecular and Cellular Endocrinology 239 (2005) 15-26.*
Sale "Models of ovarian cancer metastasis: Murine models" Drug Discovery Today: Disease Models 2006, 3, 150-154.*
Schober "New Advances in the Treatment of Metastatic Pancreatic Cancer" Digestion 2015;92:175-184.*
Boniface "Multidisciplinary management for esophageal and gastric cancer" Cancer Management and Research 2016:8 39-44.*
Gerratana "Do platinum salts fit all triple negative breast cancers?" Cancer Treatment Reviews 48 (2016) 34-41.*
Yoo "New drugs in prostate cancer" Prostate Int 4 (2016) 37-42.*
Vardiman "The World Health Organization (WHO) classification of the myeloid neoplasms" Blood (2002), 100(7), 2292-2302.*
Pui "Treatment of Acute Lymphoblastic Leukemia" New England Journal of Medicine 2006, 354, 166-78.*
Krishnan "Multiple myeloma and persistence of drug resistance in the age of novel drugs (Review)" International Journal of Oncology 49: 33-50, 2016.*
Stewart "Novel therapeutics in multiple myeloma" Hematology 2012, 17(S1), s105-s108.*
Patil et al; "2-Aryl amino-4-[4'-(benzene sulphoamiodo) -phenyl]-thiazoles"; Journal of the Indian Chemical Society, vol. 59, No. 8, Aug. 1982, pp. 1000-1001.
Kawamatsu et al.; "2-Amino-4-phenylthiazole derivatives as anti-atherogenic agents"; European Journal of Medicinal Chemistry, vol. 16, No. 4, Jul.-Aug. 1981, pp. 355-362.

* cited by examiner

SUBSTITUTED HYDROPHOBIC BENZENE SULFONAMIDE THIAZOLE COMPOUNDS FOR USE IN TREATING CANCER

FIELD OF THE INVENTION

The invention relates to new benzene sulfonamide thiazole compounds active for the treatment of cancers.

BACKGROUND OF THE INVENTION

Cutaneous melanoma deriving from the transformation of melanocytes is one of the most lethal cancers among young adults. Its incidence has increased at a dramatic rate during the last decades. Melanoma has a high capability of invasion and rapid metastasis to other organs. The prognosis of metastatic melanoma is extremely pejorative, as the various protocols of chemotherapy or immunotherapy have not shown real survival benefit. Indeed, at the ganglionic metastatic stage, the forecast deteriorates considerably with a survival rate after 5 years of 50%. At the stage of visceral metastases, the forecast is catastrophic with a median of survival of 6 months. Therefore, the melanoma, which represents only 5% of the cutaneous cancers, represents 80% of the deaths associated to this type of cancer. With an incidence, which doubles every ten years (10000 new cases in France in 2007), the melanoma constitutes a real problem of public health. Finally, even if recently encouraging results were obtained with vemurafenib and dabrafenib, two inhibitors of the B-Raf pathway, the responses remain transitory. Indeed, vemurafenib and dabrafenib target only melanomas mutated on B-Raf (approximately 50% of the metastatic melanomas). Unfortunately, after a short period of regression, the melanoma acquires in all cases, a resistance against the drug and the metastases develop again, increasing only about 2 months the life expectancy of the patient. The identification of these mechanisms of resistance is now the subject matter of numerous works but no study managed to clearly identify the mechanisms involved.

Recently, the anti-CTLA4 antibody ipilimumab able to reactivate the immune response of the patient was developed for the treatment of melanoma. However, this approach provides an objective response in only 10 to 15% of the patients.

The identification of new candidate molecules is thus a major aim for the development of specific biotherapies.

WO2014072486 describes a series of benzene sulfonamide thiazole compounds invented by the instant inventors, which are active in the treatment of cancer, especially on melanoma cells.

The inventors have now optimized the series described in WO2014072486 and generated novel hydrophobic derivatives showing a substantially higher potency in models of melanoma while having signaling pathways and mechanisms of action totally different from those of dabrafenib despite a structural similarity with dabrafenib.

In addition, it appears that the compounds of the invention are also efficient on several other cancers namely prostate, breast and colon indicating that these molecules may be active in all type of cancers.

SUMMARY OF THE INVENTION

The invention relates to benzene sulfonamide thiazole compounds of general formula:

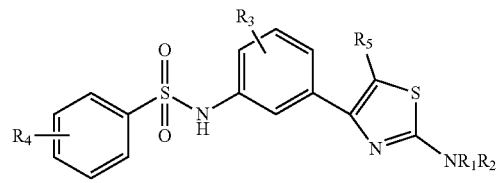

in which $R_1$ to $R_5$ have the meanings indicated below, and to processes for the preparation of, compositions containing and the uses of such derivatives.

DETAILED DESCRIPTION OF THE INVENTION

The invention relates to compounds of general formula (I):

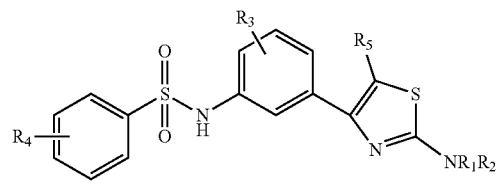

wherein
$R_1$ is selected from H, aryl and alkyl;
$R_2$ is selected from H, alkyl, aryl and CO—$R_6$;
$R_3$ is selected from H, halogen, alkyl, alkenyl, alkynyl, aryl, NHR$_7$, NR$_7$R$_8$, OR$_7$ and SR$_7$;
$R_4$ is selected from ($C_6$-$C_{12}$) alkyl, ($C_2$-$C_{12}$) alkenyl, ($C_2$-$C_{12}$) alkynyl and ($C_6$-$C_{10}$) aryl, wherein aryl is unsubstituted or substituted by 1 to 5 alkyl groups, wherein the alkyl, alkenyl and alkynyl groups are linear, branched or cyclic and wherein the alkynyl group is optionally substituted with one to three OH groups;
$R_5$ is selected from H, $R_6$, aryl, OH, OR$_6$, O-aryl, SH, SR$_6$, S-aryl, CN, NO$_2$, CF$_3$, COOR$_6$, SO$_2$NR$_7$R$_8$, CONR$_7$R$_8$, NH$_2$, NHR$_6$, NH-aryl, NR$_7$R$_8$, NHCOR$_6$ and aminoacyl;
$R_6$ is alkyl optionally substituted with halogen, OH, SH, NH$_2$, O-alkyl, S-alkyl, NH-alkyl or NH-di(alkyl);
$R_7$ and $R_8$ identical or different are H or alkyl optionally substituted with halogen, OH, SH, NH$_2$, O-alkyl, S-alkyl, NH-alkyl or NH-di (alkyl).

The invention further pertains to compounds of formula (I) above and, if appropriate, their pharmaceutically acceptable salts and/or isomers, tautomers, solvates or isotopic variations thereof for use in the treatment of cancer.

In the above general formula (I), unless specified otherwise:
Alkyl denotes a straight-chain or branched group containing 1, 2, 3, 4, 5 or 6 carbon atoms. Examples of suitable alkyl radicals are methyl, ethyl, n-propyl, isopropyl, n-butyl, isobutyl, sec-butyl, tert-butyl, n-pentyl, isopentyl, n-hexyl, etc.,
Cycloalkyl comprises 3 to 8 carbon atoms and includes cyclopropyl, cyclobutyl, cyclopentyl, cyclohexyl and cycloheptyl and cyclooctyl,
Alkenyl denotes a straight-chain or branched group containing 2, 3, 4, 5 or 6 carbon atoms and one or more double bonds. Examples of suitable alkenyl radicals are, ethenyl, n-propenyl, isopropenyl, n-butenyl, isobutenyl, sec-butenyl, tert-butenyl, n-pentenyl, isopentenyl, n-hexenyl, etc., Alkynyl denotes a straight-chain or branched group containing 2, 3, 4, 5 or 6 carbon atoms and one or more triple bonds and optionally one or more double bonds. Examples of suitable alkenyl radicals are ethynyl, n-propynyl, isopropynyl, n-butynyl, isobutynyl, sec-butynyl, tert-butynyl, n-pentynyl, isopentynyl, n-hexynyl, etc., Aryl denotes an aromatic carbon ring comprising from 6 to 10 carbon atoms. A preferred aryl group is phenyl, Aminoacyl means a group of formula $RC(NH_2)COOH$. Preferred groups are those derived from glycine, lysine, tyrosine, arginine and other natural or non-natural derivatives, The free bond on the phenyl group means that the phenyl can be substituted in the ortho, meta or para position.

In the above general formula (I), the following meanings are preferred:

$R_1$ is H,
$R_2$ is selected from H, methyl or $COCH_3$,
$R_3$ is H,
$R_4$ is ($C_6$-$C_{12}$) alkyl, preferably hexyl, heptyl, octyl, or
$R_4$ is ($C_6$-$C_{10}$ aryl), preferably phenyl or substituted phenyl, or
$R_4$ is CH=CHR$_9$, wherein $R_9$ is ($C_1$-$C_8$) alkyl, preferably hexyl, or
$R_4$ is C≡CR$_{10}$, wherein $R_{10}$ is selected from H, $C_1$-$C_8$ alkyl, hydroxy ($C_1$-$C_8$) alkyl, cyclo ($C_3$-$C_8$) alkyl and hydroxyl-cyclo ($C_3$-$C_8$ alkyl),
$R_4$ is in the meta or para position with respect to the sulfonyl group,
$R_5$ is H,
$R_6$ is alkyl,
$R_7$ and $R_8$ are H.

Preferred compounds according to the invention are the following:

N-(4-(3-(4-(oct-1-ynyl)phenylsulfonamido)phenyl)thiazol-2-yl)acetamide
N-(4-(3-(3-(oct-1-ynyl)phenylsulfonamido)phenyl)thiazol-2-yl)acetamide
N-(4-(3-(3-(3-hydroxyprop-1-ynyl)phenylsulfonamido)phenyl)thiazol-2-yl)acetamide
N-(4-(3-(3-((trimethylsilyl)ethynyl)phenylsulfonamido)phenyl)thiazol-2-yl)acetamide
N-(4-(3-(3-ethynylphenylsulfonamido)phenyl)thiazol-2-yl)acetamide
N-(3-(2-aminothiazol-4-yl)phenyl)-4-(oct-1-ynyl)benzenesulfonamide
N-(3-(2-(methylamino)thiazol-4-yl)phenyl)-4-(oct-1-ynyl)benzenesulfonamide
4-(oct-1-ynyl)-N-(3-(2-(phenylamino)thiazol-4-yl)phenyl)benzenesulfonamide
N-(4-(3-((4-(cyclohexylethynyl)phenyl)sulfonamido)phenyl)thiazol-2-yl)acetamide
N-(4-(3-([1,1'-biphenyl]-4-sulfonamido)phenyl)thiazol-2-yl)acetamide
N-(4-(3-((2,3-dihydro-1H-indene)-5-sulfonamido)phenyl)thiazol-2-yl)acetamide
N-(4-(3-((4'-methyl-[1,1'-biphenyl])-4-sulfonamido)phenyl)thiazol-2-yl)acetamide
N-(4-(3-((4-octylphenyl)sulfonamido)phenyl)thiazol-2-yl)acetamide
N-(4-(3-((4-hexylphenyl)sulfonamido)phenyl)thiazol-2-yl)acetamide
N-(4-(3-((4-(3-hydroxyprop-1-yn-1-yl)phenyl)sulfonamido)phenyl)thiazol-2-yl)acetamide
(Z)—N-(4-(3-((4-(oct-1-en-1-yl)phenyl)sulfonamido)phenyl)thiazol-2-yl)acetamide
N-(4-(3-((4-ethynylphenyl)sulfonamido)phenyl)thiazol-2-yl)acetamide.
N-(4-(4-(4-methylpiperazin-1-yl)-3-((4-pentylphenyl)sulfonamido)phenyl)thiazol-2-yl)acetamide
N-(4-(4-morpholino-3-((4-pentylphenyl)sulfonamido)phenyl)thiazol-2-yl)acetamide.

The compounds of the formula (I) may be prepared using conventional procedures such as by the following illustrative methods (schemes 1-2) in which the various substituents are as previously defined for the compounds of the formula (I) unless otherwise stated.

Scheme 1

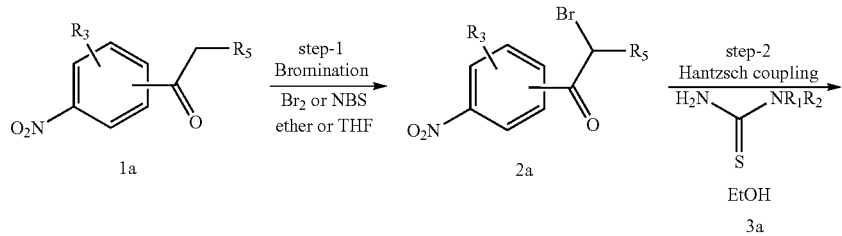

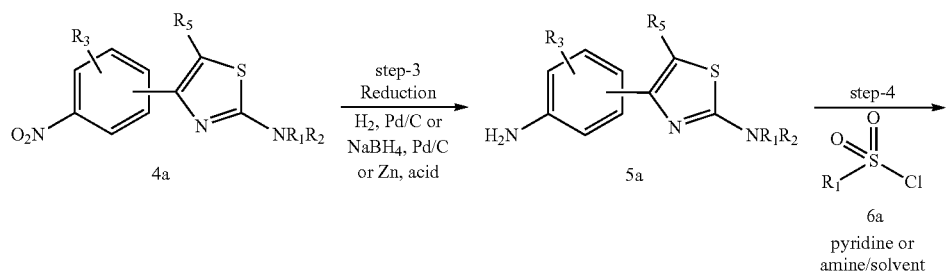

-continued

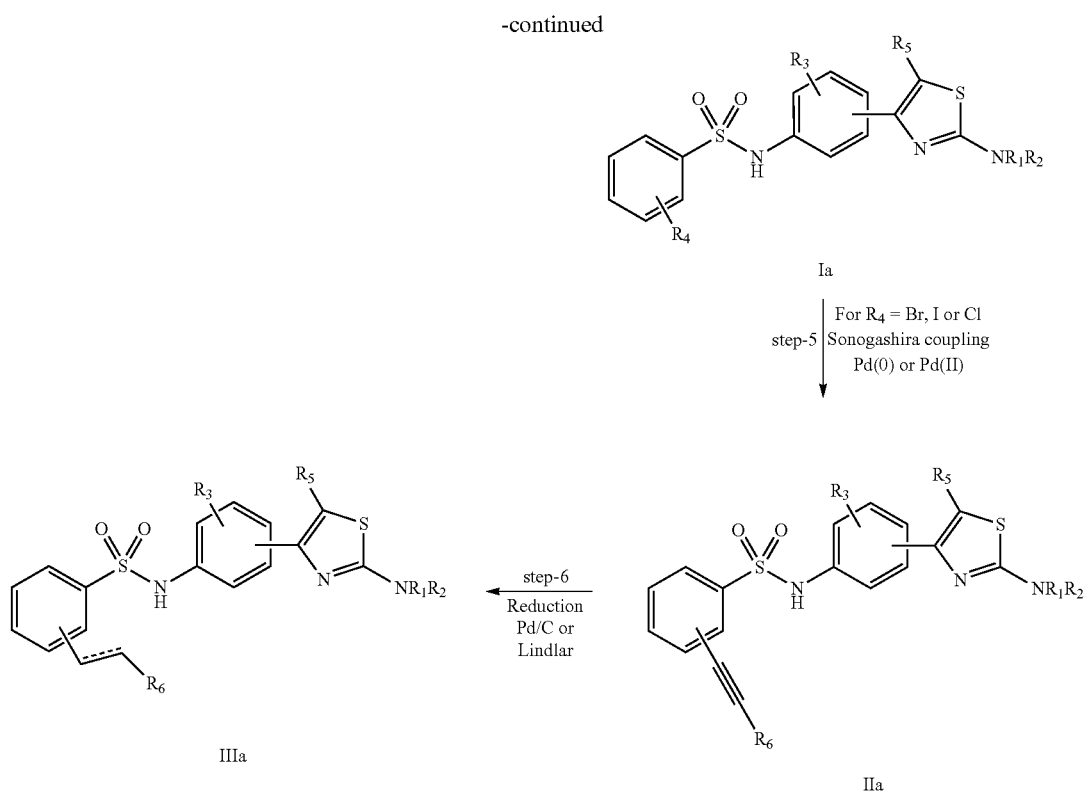

Ia

The procedure for preparing the compounds of the invention according to scheme 1 comprises the following steps:

Step 1 to prepare compound of formula 2a: by bromination of compounds of formula 1a with a suitable brominating agent $Br_2$ or N-bromosuccinimide (NBS) in solvents such as ether ($Et_2O$), THF or MeTHF, preferably in the presence of Lewis acid such as $AlCl_3$ (D. Guianvarch, R. Benhida, J-L. Fourrey, R. Maurisse, J-S. Sun. J. Chem. Soc. Chem. Comm. 2001, 1814-1815).

Step 2 to prepare compound of formula 4a: this step consists of condensing compound 2a with thiourea of formula 3 in suitable solvents that include but not restricted to EtOH, iPrOH, ethyl acetate, $CH_2Cl_2$, DMF. The reaction may be carried out at a temperature of about 25° C. to 100° C., preferably at 60-80° C. with or without acid or base catalyst depending on the reactivity of the starting material.

Step 3 to prepare compounds of formula 5a: the reduction may be carried out with a source of $H_2$ in the presence of metal catalyst which include but not limited to palladium derivatives on carbon, platinum derivatives on carbon or Raney nickel on carbon or other source of $H_2$ such as $NaBH_4/Pd/C$, metal under acidic conditions (iron, tin chloride, titanium chloride, Zinc in HCl or AcOH). The reaction could be realized in inert solvents that include but are not restricted to EtOH, MeOH, THF, dioxane, AcOH, ethylacetate, at either atmospheric or elevated pressure.

Step 4 to prepare compounds of formula Ia: the reaction is typically carried out by reacting compounds of formula 5a with sulfonyl chloride of formula 6a in an appropriate solvent such as $CH_2Cl_2$, AcOEt, DMF, DMSO, ether, THF, MeTHF, dioxane, acetonitrile in the presence of amine such as triethylamine, diisopropylethylamine, pyridine and substituted pyridines (for example DMAP). The reaction may be also carried out in pyridine as solvent.

Step 5 to prepare compounds of formula IIa: the reaction is carried out by reacting compounds of formula Ia (X=halogen, preferably I, Br and Cl) with terminal alkynes, under Sonogashira conditions, typically in the presence of palladium source, CuI, $Et_3N$, in an appropriate solvent such as DMF, DMSO, THF, MeTHF, dioxane, acetonitrile Step 6: reduction of the triple bond is performed by Lindlar-Pd—H2 or Pd/C—H2

Scheme 2

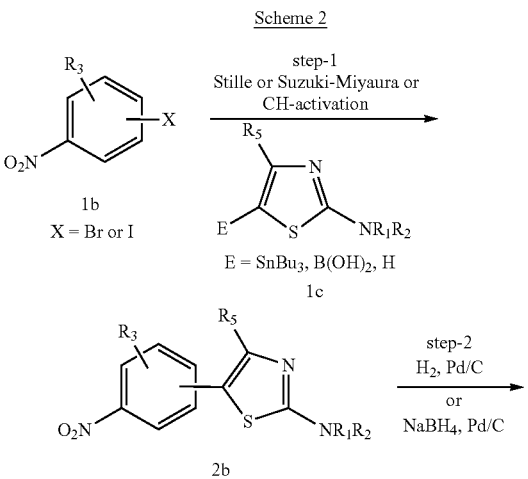

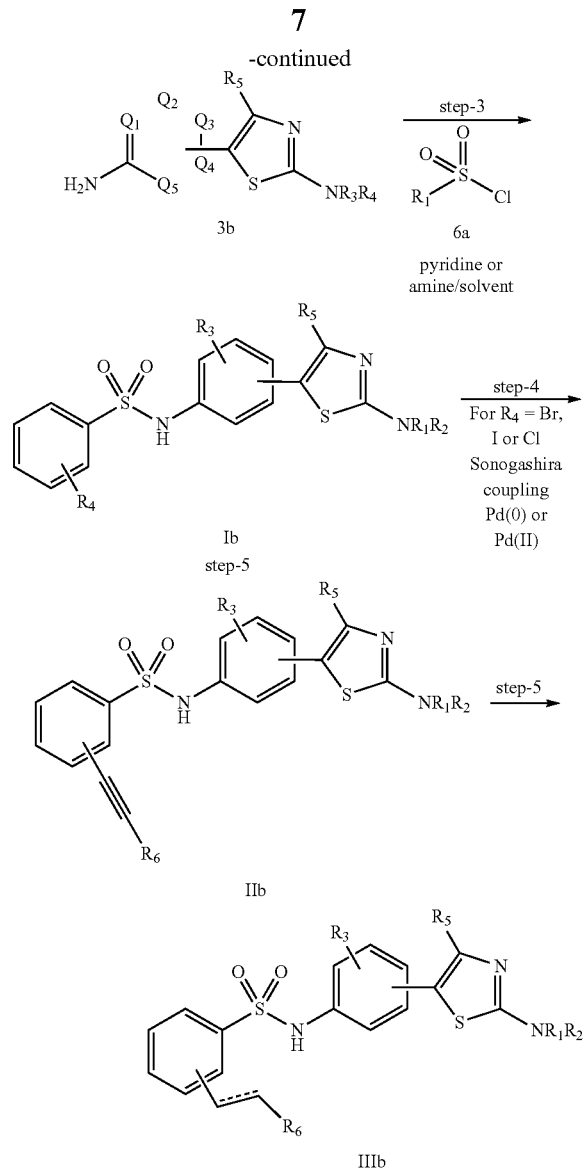

The procedure for preparing the compounds of the invention (compounds Ib, IIb and IIIb) according to scheme 2 comprises the following steps:

Step 1 to prepare compound of formula 2b: the carbon-carbon formation may be achieved using techniques conventional in the art. In a typical reaction, compound of formula 1b (X=leaving group in palladium reactions, preferably Br or I) may be reacted with boron derivatives (Suzuki-Miyaura coupling, Palladium-Catalyzed Cross-Coupling Reactions of Organoboron Compounds N. Miyaura, A. Suzuki Chem. Rev., 1995, 95 (7), pp 2457-2483), tin derivatives (Stille coupling, J. K. Stille, Angew. Chem. Int. Ed. Engl. 1986, 25, 508-524, D. Guianvarc'h, J-L Fourrey, J-S. Sun, R. Maurisse, R. Benhida. Bioorg. Med. Chem. 2003, 11, 2751-2759) or by a direct C—H activation (J. Yamaguchi, A. D. Yamaguchi, K. Itami Angew. Chem. Int. Ed. 2012, 51, 8960-9009) in an appropriate solvent for example as DMF, DMSO, THF, MeTHF, dioxane, acetonitrile, in the presence of palladium catalyst for example $Pd(PPh_3)_4$, $Pd(PPh_3)_2Cl_2$, palladium dibenzylideneacetone at a temperature of 20 to 140° C., preferably, 25-70° C. Depending on the nature of starting materials, this reaction requires some time other additives such as base (carbonate, amine) and/or ligands (phosphines) and/or copper source for example CuI or other conventional additives in the art.

Steps 2, 3, 4 and 5 in scheme 2 are similar to those described above in scheme 1, e.g., step 3, 4, 5 and 6, respectively (reduction, sulfonylation and alkylation).

Pharmaceutically acceptable salts of the compounds of formula (I) include the acid addition and base salts thereof. Suitable acid addition salts are formed from acids, which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate and xinafoate salts.

Suitable base salts are formed from bases, which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002). Pharmaceutically acceptable salts of compounds of formula (I) may be prepared by one or more of three methods:

(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water. Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components, which may be in stoichiometric or non-stoichiometric amounts. The resulting complexes may be ionised, partially ionized, or non-ionized. For a review of such complexes, see J Pharm Sci, 64 (8), 1269-1288 by Haleblian (August 1975).

Hereinafter all references to compounds of formula (I) include references to salts, solvates and complexes thereof and to solvates and complexes of salts thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As indicated, so-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H. Bundgaard (Elsevier, 1985).

Some examples of prodrugs in accordance with the invention include:

(i) where the compound of formula (I) contains a carboxylic acid functionality (—COOH), an ester thereof, for example, a compound wherein the hydrogen of the carboxylic acid functionality of the compound of formula (I) is replaced by (C1-C8)alkyl;

(ii) where the compound of formula (I) contains an alcohol functionality (—OH), an ether thereof, for example, a compound wherein the hydrogen of the alcohol functionality of the compound of formula (I) is replaced by (C1-C6)alkanoyloxymethyl; and (iii) where the compound of formula (I) contains a primary or secondary amino functionality, an amide thereof, for example, a compound wherein, as the case may be, one or both hydrogens of the amino functionality of the compound of formula (I) is/are replaced by $(C_1-C_{10})$alkanoyl.

Further examples of replacement groups in accordance with the foregoing examples and examples of other prodrug types may be found in the aforementioned references. Moreover, certain compounds of formula (I) may themselves act as prodrugs of other compounds of formula (I).

Also included within the scope of the invention are metabolites of compounds of formula (I), that is, compounds formed in vivo upon administration of the drug. Some examples of metabolites in accordance with the invention include (i) where the compound of formula (I) contains a methyl group, an hydroxymethyl derivative thereof;
(ii) where the compound of formula (I) contains a tertiary amino group, a secondary amino derivative thereof;
(iii) where the compound of formula (I) contains a secondary amino group, a primary derivative thereof;
(iv) where the compound of formula (I) contains a phenyl moiety, a phenol derivative thereof.

Compounds of formula (I) containing one or more asymmetric carbon atoms can exist as two or more stereoisomers. Included within the scope of the present invention are all stereoisomers, geometric isomers and tautomeric forms of the compounds of formula (I), including compounds exhibiting more than one type of isomerism, and mixtures of one or more thereof. Also included is acid addition or base salts wherein the counter ion is optically active, for example, d-lactate or l-lysine, or racemic, for example, dl-tartrate or dl-arginine. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or l-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC (chiral columns), on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. For reverse HPLC $CH_3CN$ and $H_2O$, MeOH or iPrOH and $H_2O$ are used as solvents. Concentration of the eluate affords the enriched mixture.

Stereoisomeric conglomerates may be separated by conventional techniques known to those skilled in the art-see, for example, "Stereochemistry of Organic Compounds" by E. L. Eliel (Wiley, New York, 1994). "Chiral Separation Techniques". by G. Subramanian. John Wiley & Sons, 2008. "Preparative Enantioselective Chromatography" by G. B. Cox. Wiley, 2005.

Pharmaceutically acceptable solvates in accordance with the invention include those wherein the solvent of crystallization may be isotopically substituted, e.g. $D_2O$.

The compounds of formula (I), their pharmaceutically acceptable salts and/or derived forms, are valuable pharmaceutically active compounds, which are suitable for the therapy and prophylaxis of various cancers, in particular melanoma, breast, prostate and colon.

Compounds of the invention may be administered as crystalline or amorphous products. They may be obtained, for example, as solid plugs, powders, or films by methods such as precipitation, crystallization, freeze-drying, spray drying, or evaporative drying. Microwave or radio frequency drying may be used for this purpose. They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form. Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Another aspect of the invention is thus a pharmaceutical composition comprising a compound as defined above and a pharmaceutically acceptable carrier.

The compounds of the invention may be administered by any suitable route.

Thus, a compound of the invention may be formulated as a pharmaceutical composition for oral, buccal, intranasal, parenteral (e.g. intravenous, intramuscular or subcutaneous), topical, or rectal administration or in a form suitable for administration by inhalation or insufflation. For oral administration, the pharmaceutical composition may take the form of, for example, a tablet or capsule prepared by conventional means with a pharmaceutically acceptable excipient such as a binding agent (e.g., pregelatinized maize starch, polyvinylpyrrolidone or hydroxypropyl methylcellulose); filler (e.g., lactose, microcrystalline cellulose or calcium phosphate); lubricant (e.g., magnesium stearate, talc or silica); disintegrant (e.g., potato starch or sodium starch glycolate); or wetting agent (e.g., sodium lauryl sulphate). The tablets may be coated by methods well known in the art. Liquid preparations for oral administration may take the form of a, for example, solution, syrup or suspension, or they may be presented as a dry product for constitution with water or other suitable vehicle before use.

Such liquid preparations may be prepared by conventional means with a pharmaceutically acceptable additive such as a suspending agent (e.g., sorbitol syrup, methyl cellulose or hydrogenated edible fats); emulsifying agent (e.g., lecithin or acacia); non-aqueous vehicle (e.g., almond oil, oily esters or ethyl alcohol); and preservative (e.g., methyl or propyl p-hydroxybenzoates or sorbic acid).

For buccal administration, the composition may take the form of tablets or lozenges formulated in conventional manner. A compound of the present invention may also be formulated for sustained delivery according to methods well known to those of ordinary skill in the art.

Examples of such formulations can be found in U.S. Pat. Nos. 3,538,214, 4,060,598, 4,173,626, 3,119,742, and 3,492,397, which are herein incorporated by reference in their entirety.

A compound of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain a formulating agent such as a suspending, stabilizing and/or dispersing agent. Alternatively, the active ingredient may be in powder form for reconstitution with a suitable vehicle, e.g., sterile pyrogen-free water, before use parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus, the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.001 mg to 5000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

According to another embodiment of the present invention, the compounds of the formula (I), or pharmaceutically acceptable salts, derived forms or compositions thereof, can also be used as a combination with one or more additional therapeutic agents to be co-administered to a patient to obtain some particularly desired therapeutic end result such as the treatment of cancers namely melanoma, breast, prostate and colon cancer.

The second and more additional therapeutic agents may also be compounds of the formula (I), or a pharmaceutically acceptable salt, derived forms or compositions thereof, or one or more compounds known in the art for the treatment of the conditions listed above. More typically, the second and more therapeutic agents will be selected from a different class of therapeutic agents.

As used herein, the terms "co-administration", "co-administered" and "in combination with", referring to the compounds of formula (I) and one or more other therapeutic agents, is intended to mean, and does refer to and include the following: simultaneous administration of such combination of compound(s) of formula (I) and therapeutic agent(s) to a patient in need of treatment, when such components are formulated together into a single dosage form which releases said components at substantially the same time to said patient, substantially simultaneous administration of such combination of compound(s) of formula (I) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (I) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (I) and therapeutic agent(s) to a patient in need of treatment, when such components are formulated together into a single dosage form which releases said components in a controlled manner whereupon they are concurrently, consecutively, and/or administered at the same and/or different times by said patient, where each part may be administered by either the same or different route. Suitable examples of other therapeutic agents which may be used in combination with the compound(s) of formula (I), or pharmaceutically acceptable salts, derived forms or compositions thereof, include, but are by no means limited to:

Anti cancer agents used for the therapy of cancers such as dacarbazine,

Nitrosourea alkylating agents, such as fotemustine

BRAF inhibitors such as vemurafenib or dabrafenib,

MEK inhibitors such as trametinib,

Anti-CTLA4 antibodies, namely ipilimumab

It is to be appreciated that all references herein to treatment include curative, palliative and prophylactic treatment. The description, which follows, concerns the therapeutic applications to which the compounds of formula (I) may be put. A still further aspect of the present invention also relates to the use of the compounds of formula (I), or pharmaceutically acceptable salts, derived forms or compositions thereof, for the manufacture of a drug having an anticancer activity. In particular, the present inventions concerns the use of the compounds of formula (I), or pharmaceutically acceptable salts, derived forms or compositions thereof, for the manufacture of a drug for the treatment of melanoma. As a consequence, the present invention provides a particularly interesting method to treat a mammal, including a human being, with an effective amount of a compound of formula (I) or a pharmaceutically acceptable salt, derived form or composition thereof. More precisely, the present invention provides a particularly interesting method for the treatment of a cancer disease in a mammal, including a human being, in particular the diseases and/or conditions listed above, comprising administering said mammal with an effective amount of a compound of formula (I), its pharmaceutically acceptable salts and/or derived forms. The following examples illustrate the preparation of the compounds of the formula (I) and their pharmacological properties

FIGURES

FIG. 1: The effect of compounds Ia-7, IIIa-3, IIIa-1, IIIa-2, IIa-2, IIa-9, Ia-4, IIa-11, IIa-12, IIa-6, compared to Ia-1, on cell viability on A375 melanoma cells.

Figure 2A:
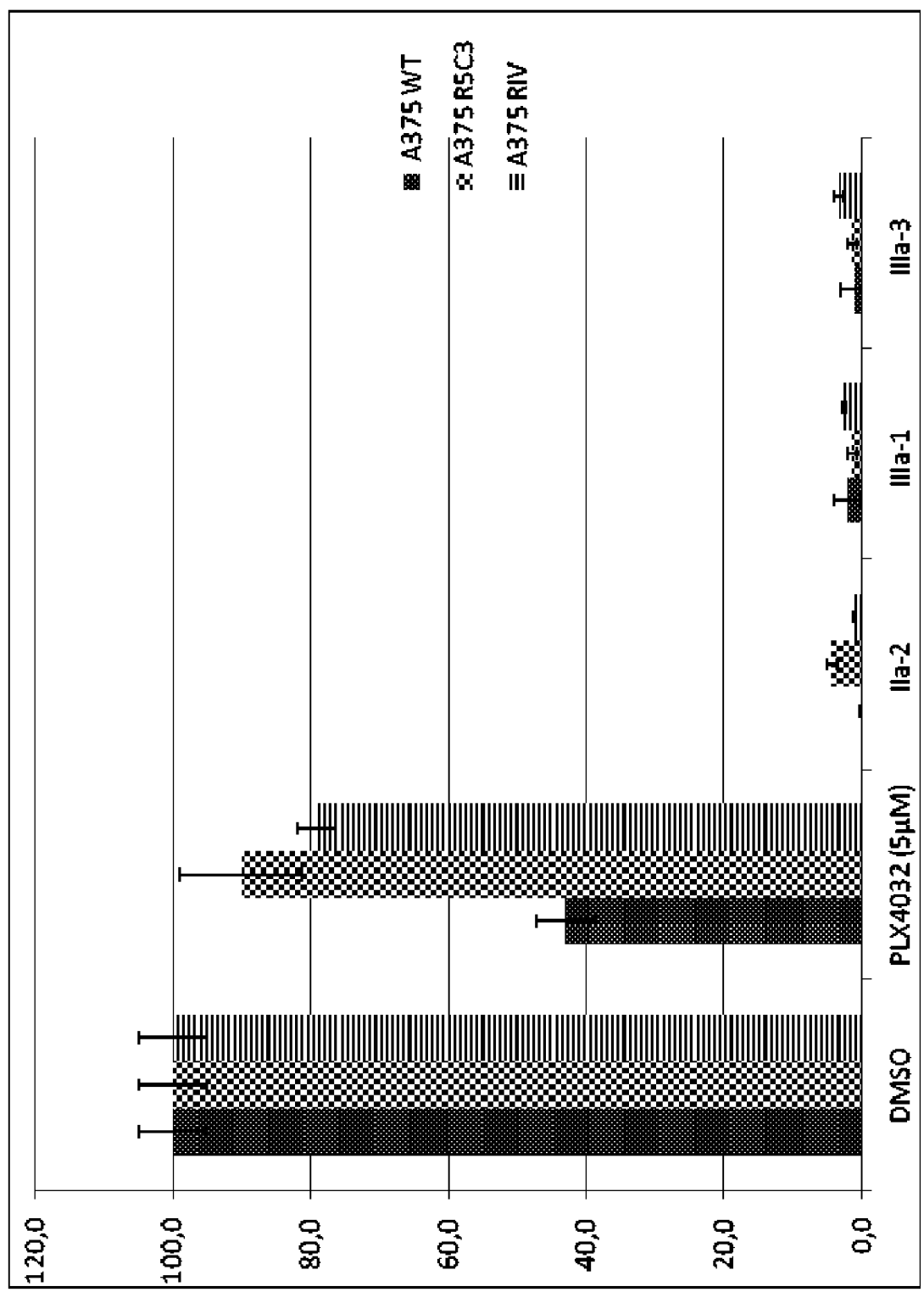

FIG. 2a: Effect of compounds IIa-2, IIIa-1 and IIIa-3 on cell viability on melanoma cells. PLX4032 was used as a positive control.

Figure 2B:
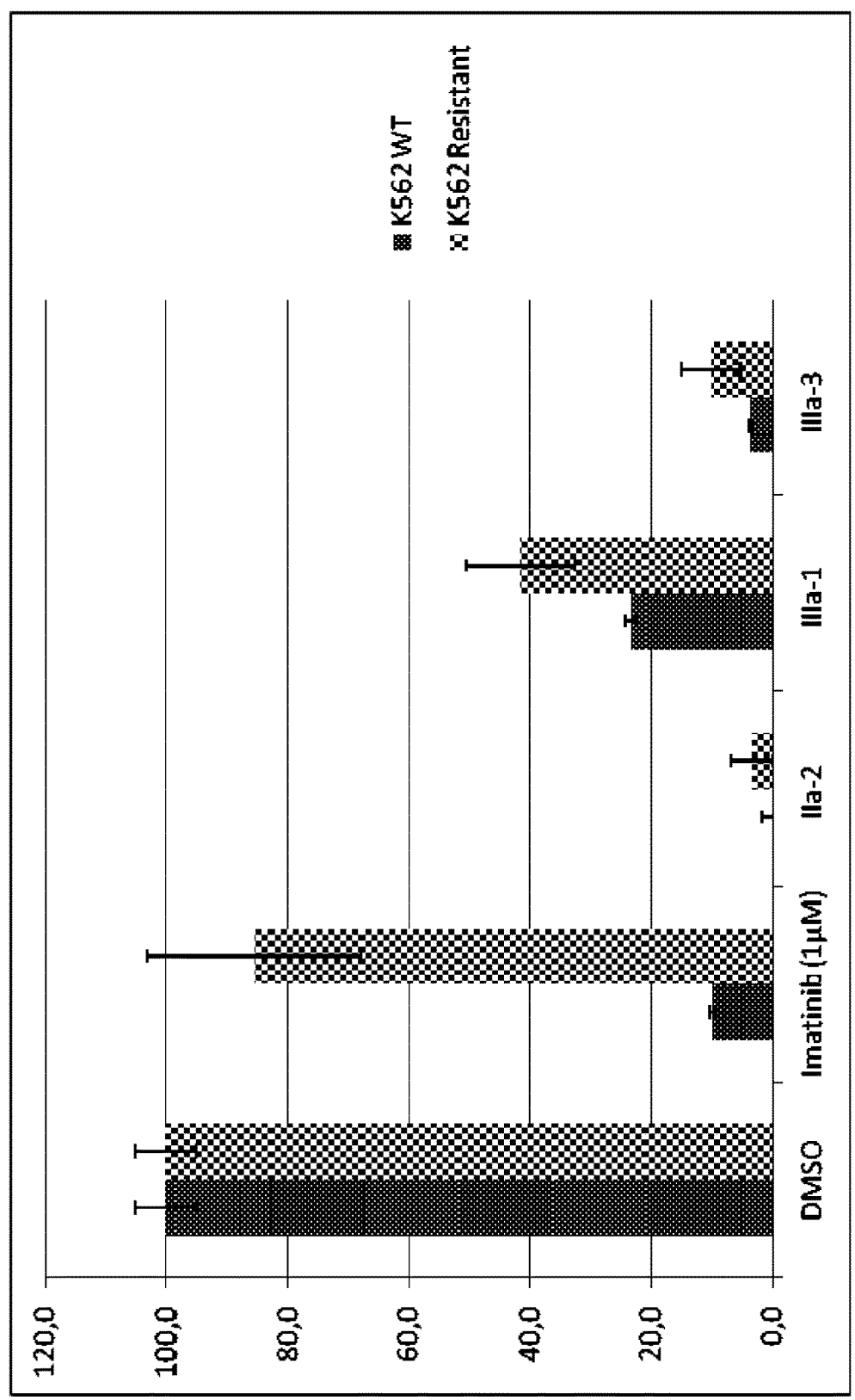

FIG. 2b: Effect of compounds IIa-2, IIIa-1 and IIIa-3 on cell viability on CML cells. Imatinib was used as a positive control.

Figure 2C:
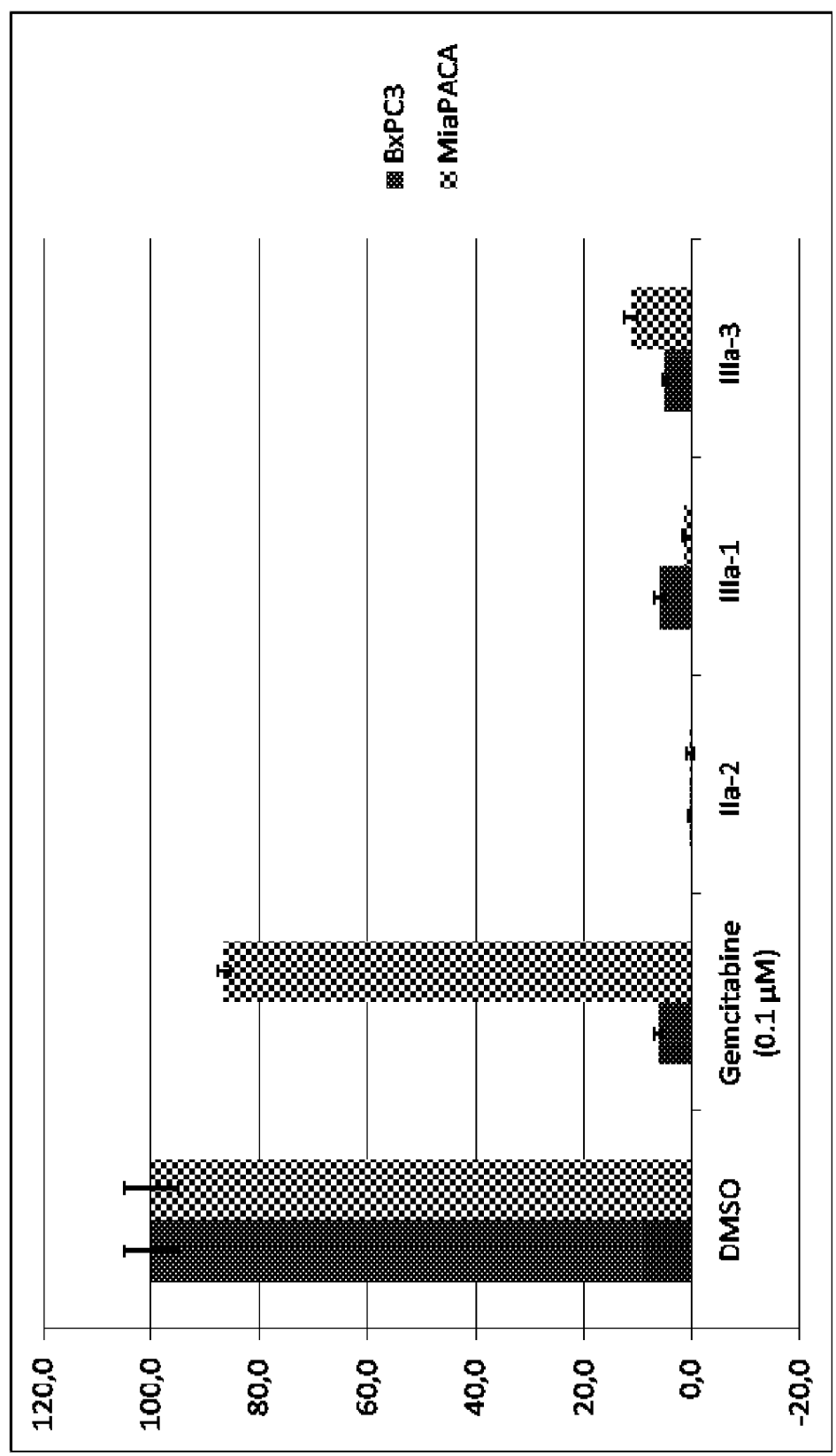

FIG. 2c: Effect of compounds IIa-2, IIIa-1 and IIIa-3 on cell viability on pancreatic cancer cells. Gemcitabine was used as a positive control.

Figure 3:
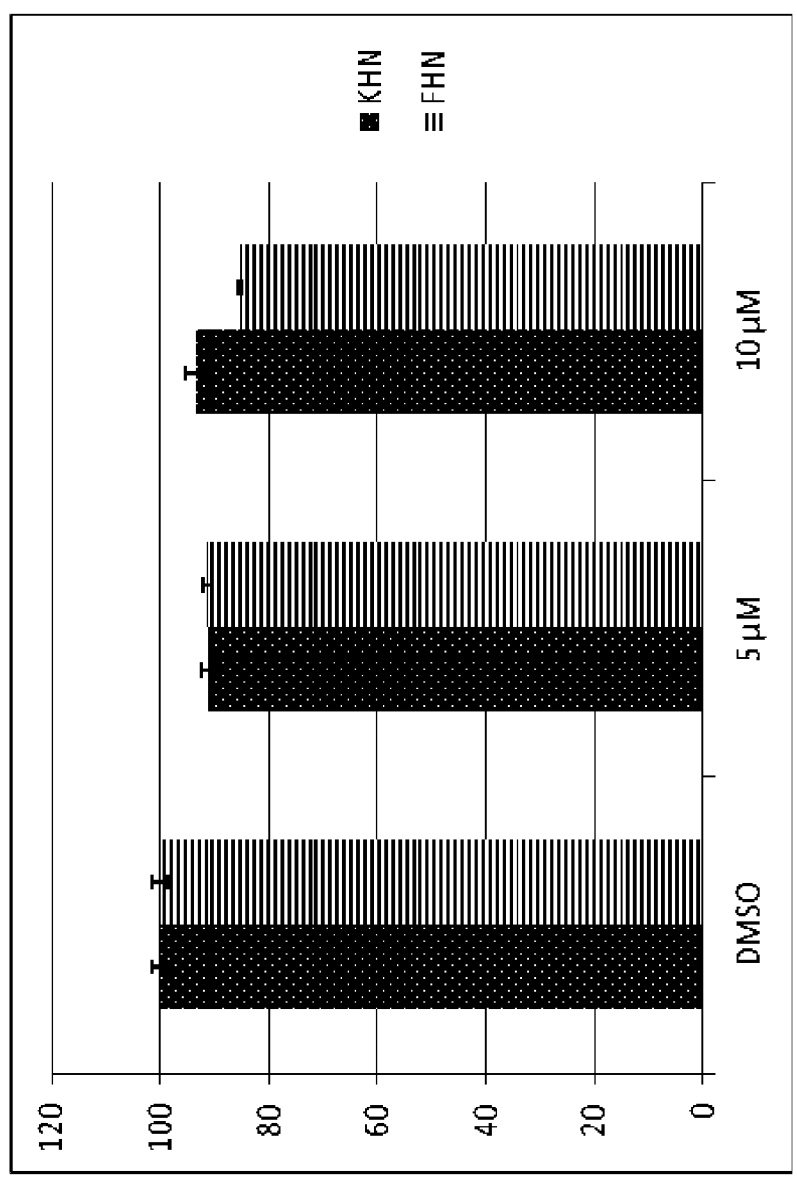

FIG. 3: Effect of compound IIa-2 on the viability of KHN and FHN cell lines.

Figure 4:
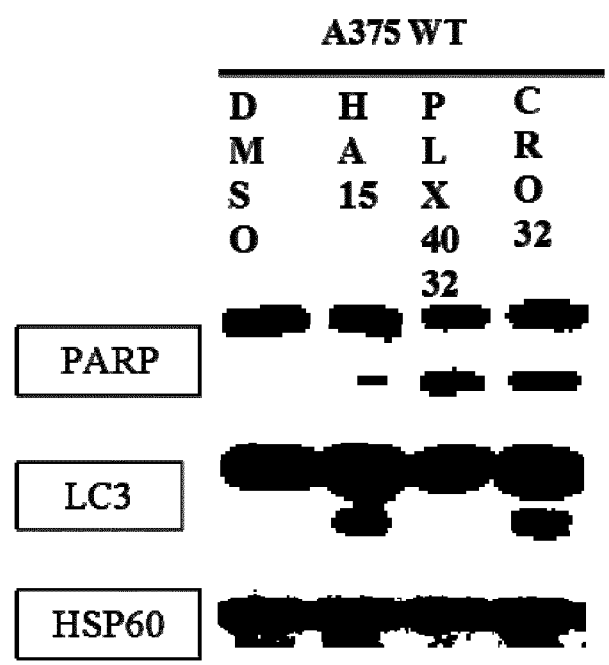

FIG. 4: Western Blots showing the mechanism of death of compound IIa-2 (apoptosis versus autophagy).

EXAMPLES

Chemical Synthesis and Characterization $^1$H and $^{13}$C NMR spectra were recorded on 200 or 500 Bruker Advance Spectrometers (200 or 500 MHz for $^1$H, 50 for $^{13}$C). Chemical shifts are expressed as parts per million from tetramethylsilane. Splitting patterns have been designated as follows: s (singlet), d (doublet), t (triplet), m (multiplet) and br (broad). Coupling constants (J values) are listed in hertz (Hz). Analytical thin-layer chromatography (TLC) was conducted on Merck (VWR) precoated silica gel 60F254 plates and compounds were visualized with ninhydrin test and/or under ultraviolet light (254 nm). Column chromatographies were carried out on silica gel (Merck, 40-63 μm). Electrospray ionization spectrometry (ESI-MS) in positive mode was performed on a Burker Daltonics (Esquire 3000 plus) apparatus. HPLC analyses were recorded on waters instruments using columns with different sizes.

HPLC Methods:

Solvent A: H$_2$O (0.1% formic acid) and solvent B: CH$_3$CN (0.1% formic acid).

Method 1: 0% B to 100% B over 10 min, 100% B for 5 min then from 100% B to 0% B over 1 min (16 min in total).

Method 2: 25% B to 100% B over 13 min, 100% B for 5 min then from 100% B to 0% B over 1 min (19 min in total).

Method 3: 25% B for 3 min then 25% B to 95% B over 5 min, 100% B for 5 min then from 100% B to 0% B over 1 min (14 min in total).

Method 4: 25% B to 100% B over 14 min, 100% B for 5 min then from 100% B to 0% B over 1 min (19 min in total).

General Procedure for the Formation of Sulfonamides (I)

To a solution of N-(4-(3-aminophenyl)thiazol-2-yl)acetamide (1 eq.) under argon in anhydrous DMF (0.1M) were added triethylamine (1.6 eq.) and the corresponding sulfonyl chloride (1.2 eq). The reaction mixture was allowed to react at r.t. until complete conversion of the starting material (from 2 h to 48 h). DMF was removed under reduced pressure and the crude material was purified by silica gel flash chromatography to afford the pure corresponding sulfonamides.

General Procedure for the Sonogashira Coupling (II)

To a suspension of halogenated derivative (Ia-3 or Ia-4) (1 eq.) in a mixture of Et$_3$N/benzene or toluene (1/1, [0.17M]) under argon were added Pd(PPh$_3$)$_4$ (15% mol.), Copper (I) iodide (15% mol.) and corresponding alkyne (5 eq.). The resulting mixture was stirred at 80° C. until complete conversion of the starting material (2 h approx.). The reaction mixture was then cooled to r.t. and all volatiles were removed under reduced pressure and the crude material was purified by silica gel flash chromatography to afford the pure corresponding coupling product.

Synthetic Procedures and Characterizations:

| Product reference | Structure |
|---|---|
| JM010 (2a-1) | 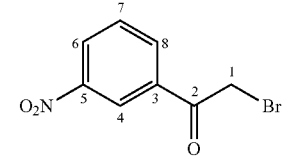 [SMILES: O=C(CBr)c1cccc([N+](=O)[O-])c1] |

2-bromo-1-(3-nitrophenyl)ethanone (2a-1)

To a suspension of commercially available 3-nitroacetophenone (4.82 g, 29.19 mmol) in anhydrous diethyl ether (25 mL) was added aluminum chloride (0.16 g, 1.20 mmol). The reaction mixture was then cooled to 0° C. before dropwise addition of bromine (1.50 mL, 29.19 mmol). The reaction was stirred for 1 h at room temperature until complete conversion of the starting material ($^1$H NMR monitoring) and quenched quickly to avoid di-brominated compound formation. After addition of water (30 mL), the mixture was extracted with diethyl ether (3×30 mL) and dried with MgSO$_4$ to afford compound 2a-1 as a yellowish brown solid (5.73 g, 97% yield). $^1$H NMR (CDCl$_3$, 200 MHz): δ 4.50 (s, 2H, H$_1$), 7.73 (t, J=8.0 Hz, 1H and H$_7$), 8.31 (ddd, J=7.8, 1.7, 1.1 Hz, 1H, H$_8$), 8.43 (ddd, J=8.2, 2.3, 1.1 Hz, 1H, H$_6$), 8.76 (t, J=1.9 Hz, 1H, H$_4$). $^{13}$C NMR (CDCl$_3$, 200 MHz): δ 30.4, 123.9, 128.2, 130.4, 134.6, 135.2, 148.6, 189.5. MS-ESI (m/z): [M+H]$^+$=244.9.

| Product reference | Structure |
|---|---|
| SBN (4a-1) | 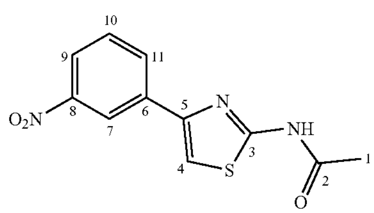 [SMILES: CC(=O)Nc1nc(-c2cccc([N+](=O)[O-])c2)cs1] |

N-(4-(3-nitrophenyl)thiazol-2-yl)acetamide (4a-1)

To a solution of 2-bromo-1-(3-nitrophenyl)ethanone (4.27 g, 17.50 mmol) in ethanol (technical grade, 150 mL) was added N-acethylthiourea (2.07 g, 17.50 mmol). The reaction mixture was heated to 80° C. for 30 minutes then allowed to cool down to room temperature. The precipitate was filtered and washed with an ice-cooled solution of 1:1 ethanol/diethyl-ether (200 mL) affording compound 4a-1 as a yellow solid (4.24 g, 92% yield). $^1$H NMR (DMSO-d$_6$, 200 MHz): δ 2.17 (s, 3H, H$_1$), 7.72 (t, J=8.2 Hz, 1H, H$_{10}$), 7.92 (s, 1H, H$_4$), 8.16 (dd, J=8.1, 2.4 Hz, 1H, H$_{11}$), 8.33 (d, J=8.1 Hz, 1H, H$_9$), 8.71 (d, J=2.1 Hz, 1H, H$_7$), 12.38 (s, 1H, NH$_{acetyl}$). $^{13}$C NMR (DMSO-d$_6$, 50 MHz): δ 22.5, 110.4, 120.0, 122.3, 130.4, 131.7, 135.8, 146.3, 148.3, 158.4, 168.8. HRMS-ESI (m/z): [M+H]$^+$ Calcd for C$_{11}$H$_{10}$O$_3$N$_3$S, 264.0437; found: 264.0439.

| Product reference | Structure |
|---|---|
| KM085 (4a-2) | 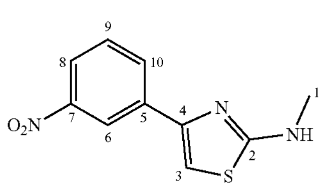 [SMILES: CNc1nc(-c2cccc([N+](=O)[O-])c2)cs1] |

N-methyl-4-(3-nitrophenyl)thiazol-2-amine (4a-2)

To a solution of 2-bromo-1-(3-nitrophenyl)ethanone (4.0 g, 16.4 mmol) in ethanol (technical grade, 150 mL) was added N-methylthiourea (1.7 g, 19.7 mmol). The reaction mixture was stirred for 2 h at r.t. and ethanol was removed under reduced pressure. The precipitate was filtered and washed with an ice-cooled (4° C.) solution of 1:1 ethanol/diethyl-ether (200 mL) affording compound 4a-2 as an orange solid (3.9 g, quant.) pure enough to carry on the synthesis. $^1$H NMR (CD$_3$OD, 200 MHz): δ 3.21 (s, 3H, H$_1$), 7.38 (s, 1H, H$_3$), 7.78 (t, J=8.1 Hz, 1H, H$_9$), 8.23-8.05 (m, 1H, H$_{10}$), 8.34 (dd, J=8.3, 2.3 Hz, 1H, H$_8$), 8.60 (t, J=2.1 Hz, 1H, H$_6$). $^{13}$C NMR (CD$_3$OD, 50 MHz): δ 33.3, 106.3, 122.5, 125.6, 131.4, 131.9, 133.8, 139.3, 150.1, 172.6. MS-ESI (m/z): [M+H]$^+$=235.9.

| Product reference | Structure |
|---|---|
| KM081 (4a-3) | 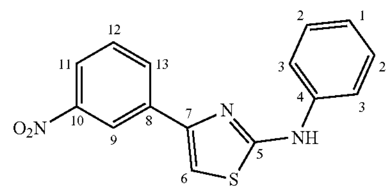 [SMILES: O=[N+]([O-])c1cccc(-c2csc(Nc3ccccc3)n2)c1] |

4-(3-nitrophenyl)-N-phenylthiazol-2-amine (4a-3)

To a solution of 2-bromo-1-(3-nitrophenyl)ethanone (4.30 g, 17.70 mmol) in ethanol (technical grade, 150 mL) was added N-phenylthiourea (2.69 g, 17.70 mmol). The reaction mixture was stirred for 2 h at r.t. and ethanol was removed under reduced pressure. The precipitate was filtered and washed with an ice-cooled (4° C.) solution of 1:1 ethanol/diethyl-ether affording compound 4a-3 as a yellow solid (5.22 g, quant.). $^1$H NMR (DMSO-d$_6$, 200 MHz): δ 7.80 (t, J=7.3 Hz, 1H, H$_{12}$), 8.17 (t, J=8.3 Hz, 2H, H$_2$), 8.64-8.43 (m, 4H, H$_1$, H$_3$ and H$_6$), 8.97 (ddd, J=8.2, 2.4, 1.0 Hz, 1H, H$_{13}$), 9.18 (dt, J=7.8, 1.3 Hz, 1H, H$_{11}$), 9.51 (t, J=2.0 Hz, 1H, H$_9$), 11.22 (s, 1H, NH$_{thiazole}$). $^{13}$C NMR (DMSO-d$_6$, 50 MHz): δ 105.7, 117.0 (2C), 119.9, 121.5, 122.1, 129.0 (2C), 130.3, 131.8, 136.0, 141.0, 147.6, 148.3, 163.6. MS-ESI (m/z): [M+H]$^+$=298.0; [M+Na]$^+$=320.0.

| Product name | Structure |
|---|---|
| DRM46-piper (5a-4) | 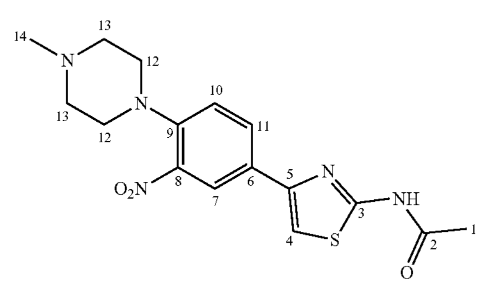 [SMILES: CC(=O)Nc1nc(-c2ccc(N3CCN(C)CC3)c([N+](=O)[O-])c2)cs1] |

N-(4-(3-nitro-4-(4-methylpiperazin-1-yl)phenyl)thiazol-2-yl)acetamide (5a-4)

To a yellow suspension of N-(4-(3-nitro-4-fluorophenyl)thiazol-2-yl)acetamide (336 mg, 1.20 mmol) in DMSO (25 mL) was added N-methylpiperazine (167 μL, 1.32 mmol). The mixture was sonicated at r.t. in the ultrasonic bath for 20 min, after which it became a limpid orange solution. Cold basic water (made with 160 mL water+40 mL saturated aq. Na$_2$CO$_3$) was added to the mixture and the product was extracted with ethyl acetate three times. The combined organic layers were dried with MgSO$_4$, and concentrated under reduced pressure to afford an orange solid corresponding to substitution product 4a-4 (412 mg, 95%). $^1$H NMR (DMSO-d$_6$, 200 MHz): δ 2.16 (s, 3H, H$_1$), 3.11-2.94 (m, 4H, H$_{13}$), 3.33 (s, 3H, H$_{14}$), 3.79-3.59 (m, 4H, H$_{12}$), 7.38 (d, J=8.7 Hz, 1H, H$_{10}$), 7.69 (s, 1H, H$_4$), 8.09 (dd, J=8.6, 2.2 Hz, 1H, H$_{11}$), 8.34 (d, J=2.1 Hz, 1H, H$_7$), 12.29 (s, 1H, NH$_{thiazole}$). $^{13}$C NMR (DMSO-d$_6$, 50 MHz): δ 22.58, 40.8, 51.3 (2C), 66.0, 108.2, 121.6, 122.5, 128.0, 130.6, 124.2, 144.4, 146.4, 158.2, 168.7. MS-ESI (m/z): [M+H]$^+$=362.5.

| Product name | Structure |
|---|---|
| DRM46-morpho (4a-5) | (structure shown) |

N-(4-(3-nitro-4-morpholinophenyl)thiazol-2-yl)acetamide (4a-5)

To a yellow suspension of N-(4-(3-nitro-4-fluorophenyl) thiazol-2-yl)acetamide (336 mg, 1.20 mmol) in DMSO (25 mL) was added morpholine (114 μL, 1.32 mmol). The mixture was sonicated at r.t. in the ultrasonic bath for 30 min, after which it became a limpid orange solution. Cold acidic water (200 mL; acidified to pH 3 using diluted aq. HCl) were added to the mixture. The orange precipitate that formed was filtered and washed with water. The solid obtained was dried at 50° C. overnight to afford pure substitution product 4a-5 (401 mg, 96%). $^1$H NMR (DMSO-d$_6$, 200 MHz): δ 2.16 (s, 3H, H$_1$), 3.03 (t, J=4.6 Hz, 4H, H$_{13}$), 3.71 (t, J=4.5 Hz, 4H, H$_{12}$), 7.38 (d, J=8.7 Hz, 1H, H$_{10}$), 7.69 (s, 1H, H$_4$), 8.09 (dd, J=8.6, 2.2 Hz, 1H, H$_{11}$), 8.34 (d, J=2.1 Hz, 1H, H$_7$), 12.29 (s, 1H, NH$_{thiazole}$). $^{13}$C NMR (DMSO-d$_6$, 50 MHz): δ 22.5, 51.3 (2C), 66.0 (2C), 108.2, 121.6, 122.6, 128.1, 130.6, 142.2, 144.4, 146.4, 158.2, 168.7. MS-ESI (m/z): [M+H]$^+$=349.5.

| Product reference | Structure |
|---|---|
| SBA (5a-1) | (structure shown) |

N-(4-(3-aminophenyl)thiazol-2-yl)acetamide (5a-1)

To a suspension of 4a-1 (2.00 g, 7.60 mmol) and 10% Pd/C (0.20 g, 10% wt.) in methanol (technical grade, 76 mL) under stirring at 0° C., was added carefully by portions sodium borohydride (1.44 g, 38.00 mmol). The reaction mixture was stirred at 0° C. until complete dissolution of sodium borohydride and was then allowed to react 3 h at r.t. After completion of the reaction monitored by TLC (CH$_2$Cl$_2$/MeOH 90:10), the mixture was filtered through a pad of Celite®, concentrated under reduced pressure and purified by silica gel flash chromatography eluted with CH$_2$Cl$_2$/MeOH (99:1 to 95:5) to afford 5a-1 as a yellow-white solid (1.47 g, 83%). $^1$H NMR (DMSO-d$_6$, 200 MHz): δ 2.16 (s, 3H, H$_1$), 5.13 (s, 2H, NH$_2$), 6.52 (dt, J=6.4, 2.5 Hz, H$_9$), 7.16-6.94 (m, 3H, H$_7$, H$_{10}$ and H$_{11}$), 7.35 (s, 1H, H$_4$), 12.22 (s, 1H, NH$_{acetyl}$). $^{13}$C NMR (DMSO-d$_6$, 50 MHz): δ 22.5, 107.0, 111.3, 113.6, 113.6, 127.2, 134.9, 148.9, 149.6, 157.6, 168.6. HRMS-ESI (m/z): [M+H]$^+$ Calcd for C$_{11}$H$_{12}$N$_3$OS, 234.0696; found: 234.0700.

| Product name | Structure |
|---|---|
| KM086 | (structure shown) |

N-methyl-4-(3-aminophenyl)thiazol-2-amine (5a-2)

To a suspension of 4a-2 (4.5 g, 19.1 mmol) and 10% Pd/C (0.45 g, 10% wt.) in methanol (technical grade, 191 mL) under stirring at 0° C., was added carefully by portions sodium borohydride (3.62 g, 95.5 mmol). The reaction mixture was stirred at 0° C. until complete dissolution of sodium borohydride and was then allowed to react 3 h at r.t. After completion of the reaction monitored by TLC (CH$_2$Cl$_2$/MeOH 90:10), the mixture was filtered through a pad of Celite®, concentrated under reduced pressure and purified by silica gel flash chromatography eluted with CH$_2$Cl$_2$/MeOH (99:1 to 95:5) to afford 5a-2 as an orange solid (1.75 g, 45%). $^1$H NMR (DMSO-d$_6$, 200 MHz): δ 2.85 (d, J=4.8 Hz, 3H, H$_1$), 5.06 (s, 2H, NH$_2$), 6.53-6.38 (m, 1H, H$_8$), 6.83 (s, 1H, H$_3$), 7.01-6.94 (m, 2H, H$_9$ and H$_{10}$), 7.09-7.03 (m, 1H, H$_6$). $^{13}$C NMR (DMSO-d$_6$, 50 MHz): δ 31.0, 99.9, 111.5, 113.1, 113.6, 128.8, 135.5, 148.6, 151.1, 169.0.

| Product reference | Structure |
|---|---|
| AM360 | 4-(3-aminophenyl)-N-phenylthiazol-2-amine (5a-3) |

To a suspension of 4a-3 (500.0 mg, 1.68 mmol) and 10% Pd/C (50.0 mg, 10% wt.) in methanol (technical grade, 35 mL) under stirring at 0° C., was added carefully by portions sodium borohydride (445.7 mg, 11.76 mmol). The reaction mixture was stirred at 0° C. until complete dissolution of sodium borohydride and was then allowed to react 3 h at r.t. After completion of the reaction monitored by TLC ($CH_2Cl_2$/MeOH 90:10), the mixture was filtered through a pad of Celite®, concentrated under reduced pressure and purified by silica gel flash chromatography eluted with $CH_2Cl_2$/MeOH (99:1 to 95:5) to afford 5a-3 as a pale yellow solid (200.5 mg, 45%). $^1$H NMR (CDCl$_3$, 200 MHz): δ 3.30 (s, 2H, NH$_2$), 6.46 (ddd, J=7.6, 2.3, 1.3 Hz, 1H, H$_{11}$), 6.58 (s, 1H, H$_6$), 7.23-6.82 (m, 8H, H$_1$, H$_2$, H$_3$, H$_9$, H$_{12}$ and H$_{13}$), 8.51 (s, 1H, NH$_{thiazole}$). $^{13}$C NMR (CDCl$_3$, 50 MHz): δ 101.8, 113.2, 114.9, 116.7, 118.4 (2C), 122.9, 129.4 (2C), 129.6, 135.6, 140.6, 146.7, 151.3, 165.2. MS-ESI (m/z): [M+H]$^+$=267.9.

| Product name | Structure |
|---|---|
| AM370 (5a-4) | 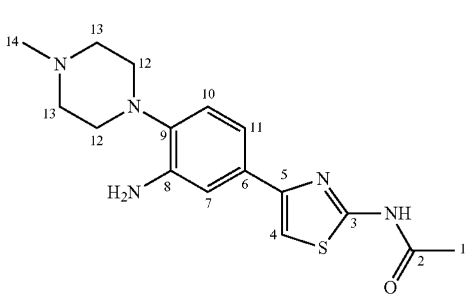 [SMILES: CC(=O)Nc1nc(-c2ccc(N3CCN(C)CC3)c(N)c2)cs1] |

N-(4-(3-amino-4-(4-methylpiperazin-1-yl)phenyl) thiazol-2-yl)acetamide (5a-4)

To a suspension of 4a-4 (300.0 mg, 0.83 mmol) and 10% Pd/C (30.0 mg, 10% wt.) in methanol (technical grade, 17 mL) under stirring at 0° C., was added carefully by portions sodium borohydride (156.9 mg, 4.15 mmol). The reaction mixture was stirred at 0° C. until complete dissolution of sodium borohydride and was then allowed to react 3 h at r.t. After completion of the reaction monitored by TLC ($CH_2Cl_2$/MeOH 90:10), the mixture was filtered through a pad of Celite®, concentrated under reduced pressure and purified by silica gel flash chromatography eluted with $CH_2Cl_2$/MeOH (3% Et$_3$N, 95:5 to 90:10) to afford 5a-4 as a brown powder (120.0 mg, 44%). $^1$H NMR (CD$_3$OD, 200 MHz): δ 2.20 (s, 3H, H$_1$), 2.44 (s, 3H, H$_{14}$), 2.76 (s, 4H, H$_{13}$), 2.97 (t, J=4.9 Hz, 4H, H$_{12}$), 6.99 (d, J=8.2 Hz, 1H, H$_{10}$), 7.15 (s, 1H, H$_4$), 7.22 (dd, J=8.2, 2.0 Hz, 1H, H$_{11}$), 7.30 (d, J=2.0 Hz, 1H, H$_7$). $^{13}$C NMR (CD$_3$OD, 50 MHz): δ 22.8, 45.9, 51.4 (2C), 56.5 (2C), 107.6, 114.4, 117.7, 120.9, 132.8, 140.0, 143.3, 151.5, 159.3, 171.0. MS-ESI (m/z): [M+H]$^+$=332.0; [M+Na]$^+$=354.0.

| Product name | Structure |
|---|---|
| CRO68 (5a-5) | 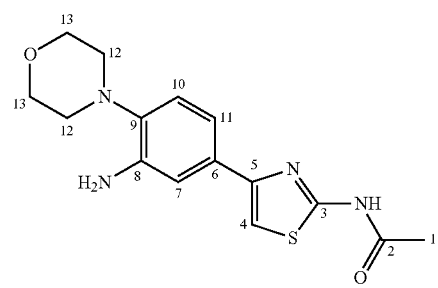 [SMILES: CC(=O)Nc1nc(-c2ccc(N3CCOCC3)c(N)c2)cs1] |

N-(4-(3-amino-4-morpholinophenyl)thiazol-2-yl) acetamide (5a-5)

To a yellow suspension of nitroaryl derivative 4a-5 (200 mg, 0.574 mmol) in methanol (technical grade, 20 mL) was added Pd/C (30 mg, 10% wt.), then sodium borohydride (130 mg, 3.44 mmol). The mixture was stirred at r.t. for 1 h after which it became a dark green suspension. The mixture was filtered through Celite® and the filtrate was evaporated. The residue was partitioned between diluted aq. Na$_2$CO$_3$ and ethyl acetate. The aqueous phase was extracted with ethyl acetate twice. The combined organic layers were dried with MgSO$_4$, and concentrated under reduced pressure. Purification by flash chromatography ($CH_2Cl_2$:CH$_3$OH, 100:0 to 94:6) afforded the pure desired aniline 5a-5 as a pale yellow solid (165.5 mg, 91%). $^1$H NMR (DMSO-d$_6$, 200 MHz): δ 2.16 (s, 3H, H$_1$), 2.99-2.69 (m, 4H, H$_{12}$), 3.74 (dd, J=5.8, 3.1 Hz, 4H, H$_{13}$), 4.85 (s, 2H, NH$_2$), 6.89 (d, J=8.2 Hz, 1H, H$_{10}$), 7.09 (dd, J=8.1, 2.0 Hz, 1H, H$_{11}$), 7.22 (d, J=6.5 Hz, 2H, H$_4$ and H$_7$), 12.21 (s, 1H, NH$_{thiazole}$). $^{13}$C NMR (DMSO-d$_6$, 50 MHz): δ 22.5, 50.9 (2C), 66.6 (2C), 106.0, 111.9, 114.6, 119.1, 130.3, 137.9, 142.2, 149.5, 157.6, 168.5. MS-ESI (m/z): [M+H]$^+$=319.0; [M+Na]$^+$=341.0.

| Product ref | Structure |
|---|---|
| JG28-F4 (Ia-1) | 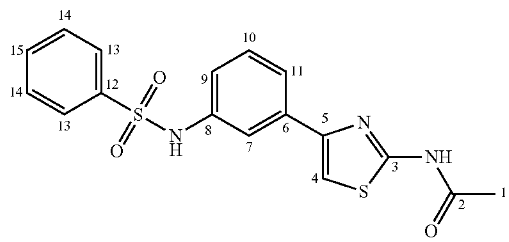 [SMILES: CC(=O)Nc1nc(-c2cccc(NS(=O)(=O)c3ccccc3)c2)cs1] |

N-(4-(3-(phenylsulfonamido)phenyl)thiazol-2-yl) acetamide (Ia-1)

The general procedure for the formation of sulfonamides (I) was followed using 5a-1 (102 mg, 0.44 mmol), benzenesulfonyl chloride (67.6 μL, 0.53 mmol) as reagents and triethylamine. Purification by silica gel flash chromatography (CH$_2$Cl$_2$:EtOAc; 100:0 to 80:20) afforded the titled compound as a white fine powder (28.8 mg, 37%). $^1$H NMR (Acetone-d$_6$, 200 MHz): δ 2.28 (s, 3H, H$_1$), 7.10 (ddd, J=8.0, 2.2, 1.1 Hz, 1H, H$_9$), 7.30-7.20 (m, 1H, H$_{10}$), 7.37 (s, 1H, H$_4$), 7.64-7.46 (m, 4H, H$_{11}$, H$_{14}$ and H$_{15}$), 7.90-7.79 (m, 3H, H$_7$ and H$_{13}$), 9.12 (s, 1H, NH$_{sulfonamide}$), 11.21 (s, 1H, NH$_{acetyl}$). $^{13}$C NMR (Acetone-d$_6$, 50 MHz): δ 22.5, 108.5, 117.6, 119.7, 121.6, 126.7 (2C), 129.3 (2C), 129.5, 132.9, 135.3, 138.2, 139.5, 148.1, 158.0, 168.7. HRMS-ESI (m/z): [M+H]$^+$ Calcd for C$_{17}$H$_{16}$N$_3$O$_3$S$_2$, 374.0628; Found: 374.0627.

| Product ref | Structure |
|---|---|
| JG25 (Ia-2) | 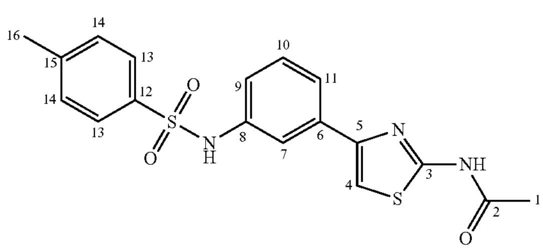 [SMILES: CC(=O)Nc1nc(-c2cccc(NS(=O)(=O)c3ccc(C)cc3)c2)cs1] |

N-(4-(3-((4-methylphenyl)sulfonamido)phenyl)thiazol-2-yl)acetamide (Ia-2)

The general procedure for the formation of sulfonamides (I) was followed using 5a-1 (102 mg, 0.44 mmol), tosyl chloride (101.0 mg, 0.53 mmol) as reagents and triethylamine. Purification by silica gel flash chromatography (CH$_2$Cl$_2$:EtOAc; 100:0 to 80:20) afforded the titled compound as a white powder (122.7 mg, 72%). $^1$H NMR (Acetone-d$_6$, 200 MHz): δ 2.28 (s, 3H, H$_1$), 2.33 (s, 3H, H$_{16}$), 7.10 (ddd, J=8.0, 2.2, 1.1 Hz, 1H, H$_9$), 7.34-7.20 (m, 3H, H$_{10}$ and H$_{14}$), 7.37 (s, 1H, H$_4$), 7.59 (ddd, J=7.7, 1.6, 1.1 Hz, 1H, H$_{11}$), 7.75-7.66 (m, 2H, H$_{13}$), 7.87 (ddd, J=2.2, 1.6, 0.5 Hz, 1H, H$_7$), 9.04 (s, 1H, NH$_{sulfonamide}$), 11.17 (s, 1H, NH$_{acetyl}$). $^{13}$C NMR (Acetone-d$_6$, 50 MHz): δ 20.9, 22.5, 108.4, 117.4, 119.5, 121.5, 126.7 (2C), 129.5, 129.7 (2C), 135.2, 136.6, 138.3, 143.3, 148.2, 158.1, 168.8. HRMS-ESI (m/z): [M+H]$^+$ Calcd for C$_{18}$H$_{18}$N$_3$O$_3$S$_2$, 388.0784; Found: 388.0788.

| Product ref | Structure |
|---|---|
| CRO51 (Ia-3) | 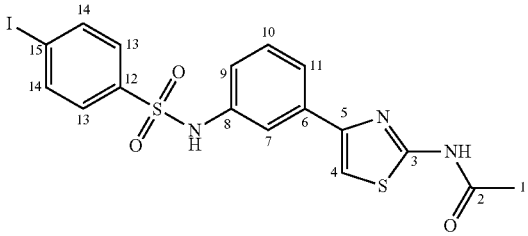 [SMILES: CC(=O)Nc1nc(-c2cccc(NS(=O)(=O)c3ccc(I)cc3)c2)cs1] |

N-(4-(3-((4-iodophenyl)sulfonamido)phenyl)thiazol-2-yl)acetamide (Ia-3)

The general procedure for the formation of sulfonamides (I) was followed using 5a-1 (1.50 g, 6.44 mmol), 4-iodobenzenesulfonyl chloride (2.33 g, 7.73 mmol) as reagents and triethylamine. Purification by silica gel flash chromatography ($CH_2Cl_2$:EtOAc; 100:0 to 70:30) afforded the titled compound as a white powder (1.85 g, 60%). $^1$H NMR (DMSO-$d_6$, 200 MHz): δ 2.17 (s, 3H, $H_1$), 7.05-6.96 (m, 1H, $H_9$), 7.27 (t, J=7.9 Hz, 1H, $H_{10}$), 7.62-7.45 (m, 3H, $H_4$, $H_{11}$ and $H_{14}$), 7.69 (t, J=1.9 Hz, 1H, $H_7$), 7.99-7.88 (m, 1H, $H_{13}$), 10.45 (s, 1H, $NH_{sulfonamide}$), 12.26 (s, 1H, $NH_{acetyl}$). $^{13}$C NMR (DMSO-$d_6$, 50 MHz): δ 22.5, 101.2, 108.5, 117.7, 119.8, 121.8, 128.3 (2C), 129.6, 135.3, 137.9, 138.2 (2C), 139.0, 148.0, 158.0, 168.7. HRMS-ESI (m/z): [M+H]$^+$ Calcd for $C_{17}H_{15}IN_3O_3S_2$, 499.9594; Found: 499.9591.

| Product ref | Structure |
|---|---|
| CRO48 (Ia-4) | 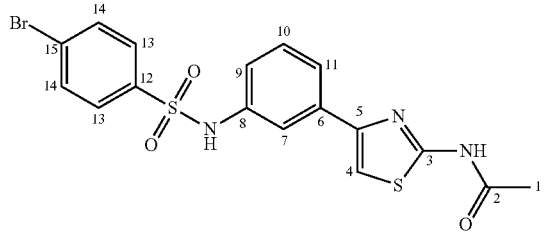 [SMILES: CC(=O)Nc1nc(-c2cccc(NS(=O)(=O)c3ccc(Br)cc3)c2)cs1] |

N-(4-(3-((4-bromophenyl)sulfonamido)phenyl)thiazol-2-yl)acetamide (Ia-4)

The general procedure for the formation of sulfonamides (I) was followed using 5a-1 (1.00 g, 4.29 mmol), 4-bromobenzenesulfonyl chloride (1.20 g, 4.72 mmol) as reagents and triethylamine. Purification by silica gel flash chromatography ($CH_2Cl_2$:EtOAc; 100:0 to 70:30) afforded the titled compound as a white powder (1.49 g, 77%). $R_f$(EtOAc/cyclohexane, 1/1, v/v)=0.44. $^1$H NMR (CD$_3$OD, 200 MHz): δ 2.22 (s, 3H, $H_1$), 7.06-6.92 (m, 1H, $H_9$), 7.31-7.10 (m, 2H, $H_{10}$ and $H_4$), 7.73-7.46 (m, 6H, $H_7$, $H_{11}$, $H_{13}$, $H_{14}$ and $H_{15}$). $^{13}$C NMR (CD$_3$OD, 50 MHz): δ 21.9, 107.9, 118.6, 120.2, 122.3, 127.3 (2C), 128.3, 129.2 (2C), 131.9, 135.4, 137.2, 138.3, 148.7, 158.0, 169.3. HRMS-ESI (m/z): [M+H]$^+$ Calcd for $C_{17}H_{15}O_3N_3BrS_2$, 451.9733; Found: 451.9745.

| Product ref | Structure |
|---|---|
| AM77 (Ia-5) | 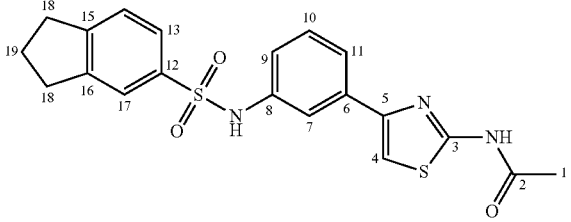 |

N-(4-(3-((2, 3-dihydro-1H-indene)-5-sulfonamido)phenyl)thiazol-2-yl)acetamide (Ia-5)

The general procedure for the formation of sulfonamide (I) was followed using 5a-1 (75 mg, 0.32 mmol), indane-5-sulfonyl chloride (83.0 mg, 0.39 mmol) as reagents and triethylamine. Purification by silica gel flash chromatography ($CH_2Cl_2$:EtOAc; 100:0 to 80:20) afforded the titled compound as a white powder (98 mg, 74%). $^1$H NMR (DMSO-$d_6$, 200 MHz): δ 1.96 (p, J=7.4 Hz, 2H, $H_{19}$), 2.14 (s, 3H, $H_1$), 2.82 (t, J=7.4 Hz, 4H, $H_{18}$), 7.01 (d, J=8.9 Hz, 1H, $H_9$), 7.38-7.17 (m, 2H, $H_{10}$ and $H_{14}$), 7.76-7.41 (m, 5H, $H_4$, $H_7$, $H_{11}$, $H_{13}$ and $H_{17}$), 10.29 (s, 1H, $NH_{sulfonamide}$), 12.25 (s, 1H, $NH_{acetyl}$). $^{13}$C NMR (DMSO-$d_6$, 50 MHz): δ 22.5, 24.9, 32.0, 108.4, 117.2, 119.2, 121.3, 122.4, 124.8, 125.0, 129.5, 135.2, 135.2, 137.5, 138.4, 145.0, 148.1, 149.5, 158.0, 168.7. HRMS-ESI (m/z): $[M+H]^+$ Calcd for $C_{20}H_{20}N_3O_3S_2$, 414.0941; Found: 414.0938.

| Product name | Structure |
|---|---|
| AM69 (Ia-6) | 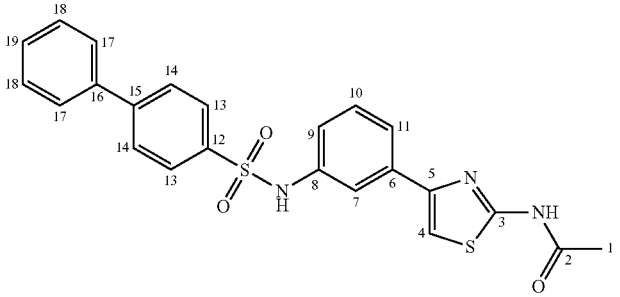 [SMILES: CC(=O)Nc1nc(-c2cccc(NS(=O)(=O)c3ccc(-c4ccccc4)cc3)c2)cs1] |

N-(4-(3-([1,1'-biphenyl]-4-sulfonamido)phenyl)thiazol-2-yl)acetamide (Ia-6)

The general procedure for the formation of sulfonamide (I) was followed using 5a-1 (100 mg, 0.43 mmol), biphenyl-4-sulfonyl chloride (130.0 mg, 0.51 mmol) as reagents and triethylamine. Purification by silica gel flash chromatography ($CH_2Cl_2$:EtOAc; 80:20 to 60:40) afforded the titled compound as a white powder (85.1 mg, 43%). $^1$H NMR (Acetone-$d_6$, 200 MHz): δ 2.28 (s, 3H, $H_1$), 7.19-7.10 (m, 1H, $H_9$), 7.28 (t, J=7.8 Hz, 1H, $H_{10}$), 7.54-7.37 (m, 4H, $H_4$, $H_{19}$ and $H_{18}$), 7.73-7.58 (m, 3H, $H_{11}$ and $H_{17}$), 7.94-7.76 (m, 5H, $H_7$, $H_{13}$ and $H_{14}$). $^{13}$C NMR (DMSO-$d_6$, 50 MHz): δ 22.5, 108.5, 117.5, 119.5, 121.6, 127.1 (2C), 127.3 (2C), 127.4 (2C), 128.6, 129.1 (2C), 129.6, 135.3, 138.2, 138.2, 138.3, 144.3, 148.1, 158.0, 168.7. HRMS-ESI (m/z): $[M+H]^+$ Calcd for $C_{23}H_{20}N_3O_3S_2$, 450.0941; Found: 450.0935.

| Product name | Structure |
|---|---|
| AM107 (Ia-7) | 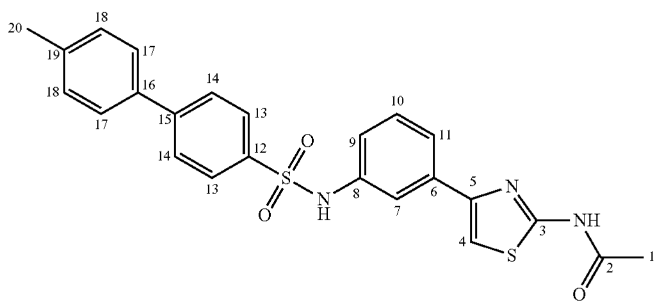 [SMILES: CC(=O)Nc1nc(-c2cccc(NS(=O)(=O)c3ccc(-c4ccc(C)cc4)cc3)c2)cs1] |

N-(4-(3-((4'-methyl-[1,1'-biphenyl])-4-sulfonamido)phenyl)thiazol-2-yl)acetamide (Ia-7)

The general procedure for the formation of sulfonamide (I) was followed using 5a-1 (102 mg, 0.44 mmol), 4'-methylbiphenyl-4-sulfonyl chloride (205.0 mg, 0.77 mmol) as reagents and triethylamine Purification by silica gel flash chromatography ($CH_2Cl_2$:EtOAc; 100:0 to 70:30) afforded the titled compound as a white powder (110.5 mg, 37%). $^1$H NMR (Acetone-$d_6$, 200 MHz): δ 2.27 (s, 3H, $H_1$), 2.34 (s, 3H, $H_{20}$), 7.19-7.12 (m, 1H, $H_9$), 7.31-7.22 (m, 3H, $H_{10}$ and $H_{18}$), 7.38 (s, 1H, $H_4$), 7.65-7.49 (m, 3H, $H_{11}$ and $H_{17}$), 7.81-7.71 (m, 2H, $H_{14}$), 7.97-7.80 (m, 3H, $H_7$ and $H_{13}$). $^{13}$C NMR (Acetone-$d_6$, 50 MHz): δ 21.1, 22.9, 108.8, 119.3, 121.0, 122.9, 127.9 (2C), 128.0 (2C), 128.7 (2C), 130.3, 130.6 (2C), 136.8, 137.0, 139.3 (2C), 139.3, 146.0, 149.8, 159.0, 169.2. HRMS-ESI (m/z): [M+H]$^+$ Calcd for $C_{24}H_{22}N_3O_3S_2$, 464.1097; Found: 464.1093.

| Product ref | Structure |
|---|---|
| CRO46 (Ia-8) | 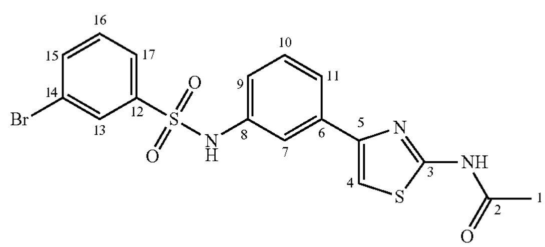 [SMILES: CC(=O)Nc1nc(-c2cccc(NS(=O)(=O)c3cccc(Br)c3)c2)cs1] |

N-(4-(3-((3-bromophenyl)sulfonamido)phenyl)thiazol-2-yl)acetamide (Ia-8)

The general procedure for the formation of sulfonamide (I) was followed using 5a-1 (583 mg, 2.50 mmol), 3-bromobenzenesulfonyl chloride (405 µL, 2.80 mmol) as reagents and triethylamine. Purification by silica gel flash chromatography (cyclohexane:EtOAc; 100:0 to 50:50) to afforded the titled compound as a white powder (991 mg, 88%). $R_f$(EtOAc/cyclohexane, 1/1, v/v)=0.45. $^1$H NMR ($CDCl_3$-$CD_3OD$ (1:1), 200 MHz): δ 2.21 (s, 3H, $H_1$), 7.01 (ddd, J=8.0, 2.3, 1.1 Hz, 1H, $H_9$), 7.12 (s, 1H, $H_4$), 7.26 (dt, J=10.3, 7.9 Hz, 2H, $H_{10}$ and $H_{16}$), 7.72-7.43 (m, 4H, $H_{11}$, $H_7$, $H_{15}$ and $H_{17}$), 7.92 (t, J=1.9 Hz, 1H, $H_{13}$). $^{13}$C NMR ($CDCl_3$-$CD_3OD$ (1:1), 50 MHz): δ 21.8, 107.9, 118.7, 120.2, 122.3, 122.4, 125.3, 129.2, 129.5, 130.2, 135.4, 135.4, 137.1, 141.1, 148.6, 158.0, 169.3. HRMS-ESI (m/z): [M+H]$^+$ Calcd for $C_{17}H_{15}BrN_3O_2S_2$, 451.9733; Found: 451.9745.

| Product ref | Structure |
|---|---|
| AM359 (Ia-9) | 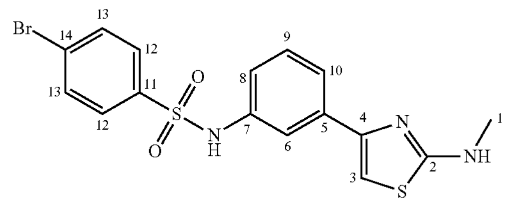 [SMILES: CNc1nc(-c2cccc(NS(=O)(=O)c3ccc(Br)cc3)c2)cs1] |

4-bromo-N-(3-(2-(methylamino)thiazol-4-yl)phenyl) benzenesulfonamide (Ia-9)

The general procedure for the formation of sulfonamides (I) was followed using 5a-2 (500.0 mg, 2.43 mmol), 4-bromobenzenesulfonyl chloride (685.5 mg, 2.68 mmol) as reagents and triethylamine. Purification by silica gel flash chromatography (CH$_2$Cl$_2$:EtOAc; 100:0 to 70:30) afforded the titled compound as a white powder (376.8 mg, 37%). $^1$H NMR (Acetone-d$_6$, 200 MHz): δ 2.97 (s, 1H, H$_1$), 6.87 (s, 2H, H$_3$ and NH$_{thiazole}$), 7.13 (ddd, J=7.9, 2.0, 1.1 Hz, 1H, H$_8$), 7.24 (t, J=7.8 Hz, 1H, H$_9$), 7.59 (d, J=7.7 Hz, 1H, H$_{10}$), 7.84-7.64 (m, 4H, H$_{12}$ and H$_{13}$), 8.00 (s, 1H, H$_6$), 9.35 (s, 1H, NH$_{sulfonamide}$). $^{13}$C NMR (Acetone-d$_6$, 50 MHz): δ 31.8, 102.1, 119.7, 120.7, 123.2, 127.9, 130.0 (2C), 130.1, 133.2 (2C), 137.5, 138.7, 140.3, 151.4, 170.7. MS-ESI (m/z): [M+H]$^+$=424.0.

| Product ref | Structure |
|---|---|
| AM363 (Ia-10) | 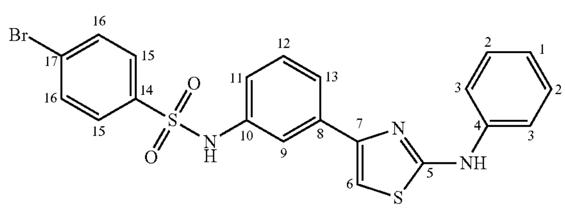 [SMILES: O=S(=O)(Nc1cccc(-c2csc(Nc3ccccc3)n2)c1)c1ccc(Br)cc1] |

4-bromo-N-(3-(2-(phenylamino)thiazol-4-yl)phenyl) benzenesulfonamide (Ia-10)

The general procedure for the formation of sulfonamides (I) was followed using 5a-3 (151.0 mg, 0.57 mmol), 4-bromobenzenesulfonyl chloride (161.0 mg, 0.63 mmol) as reagents and triethylamine. Purification by silica gel flash chromatography (CH$_2$Cl$_2$:EtOAc; 100:0 to 70:30) afforded the titled compound as a white powder (135.2 mg, 49%). $^1$H NMR (Acetone-d$_6$, 200 MHz): δ 7.01 (t, J=7.4 Hz, 1H, H$_{12}$), 7.22-7.07 (m, 2H, H$_{11}$ and H$_6$), 7.42-7.25 (m, 3H, H$_1$ and H$_2$), 7.85-7.62 (m, 7H, H$_3$, H$_{15}$, H$_{16}$ and H$_{13}$), 7.93 (t, J=1.9 Hz, 1H, H$_9$), 9.20 (s, 1H, NH$_{sulfonamide}$), 9.36 (s, 1H, NH$_{thiazole}$). $^{13}$C NMR (Acetone-d$_6$, 50 MHz): δ 103.8 (2C), 118.3 (2C), 119.6, 120.9, 122.6, 123.1, 128.0, 129.9 (2C), 130.0, 133.2 (2C), 137.1, 138.9, 140.2, 142.4, 151.3, 164.5. MS-ESI (m/z): [M+H]$^+$=486.0; [M+Na]$^+$=508.0

| Product ref | Structure |
|---|---|
| AM371 (Ia-11) | (structure diagram) |

N-(4-(4-(4-methylpiperazin-1-yl)-3-((4-pentylphenyl)sulfonamido)phenyl)thiazol-2-yl) acetamide (Ia-11)

The general procedure for the formation of sulfonamide (I) was followed using 5a-4 (72.1 mg, 0.22 mmol), 4-pentylphenylsulfonyl chloride (59.2 mg, 0.24 mmol) as reagents and triethylamine Purification by silica gel flash chromatography (CH$_2$Cl$_2$:CH$_3$OH; 95:5 to 90:10) afforded the titled compound as a white powder (78.5 mg, 68%). $^1$H NMR (CD$_3$OD, 200 MHz): δ 0.84 (t, J=6.8 Hz, 3H, H$_{23}$), 1.36-1.10 (m, 4H, H$_{21}$ and H$_{22}$), 1.51 (quint., J=7.5 Hz, 2H, H$_{20}$), 2.22 (s, 3H, H$_1$), 2.33 (s, 3H, H$_{14}$), 2.67-2.41 (m, 10H, H$_{12}$, H$_{13}$ and H$_{19}$), 7.13 (d, J=8.3 Hz, 1H, H$_{10}$), 7.24 (t, J=4.1 Hz, 3H, H$_4$ and H$_{17}$), 7.56 (dd, J=8.3, 2.0 Hz, 1H, H$_{11}$), 7.75-7.62 (m, 2H, H$_{16}$), 8.17 (d, J=2.0 Hz, 1H, H$_7$). $^{13}$C NMR (CD$_3$OD, 50 MHz): δ 14.5, 22.8, 23.6, 32.1, 32.5, 36.7, 46.2, 53.2 (2C), 56.5 (2C), 108.9, 119.8, 123.4, 124.0, 128.3 (2C), 130.3 (2C), 133.9, 134.6, 138.4, 144.2, 150.4, 150.5, 159.6, 171.0. MS-ESI (m/z): [M+H]$^+$=542.2; [M+Na]=564.2.

| Product name | Structure |
|---|---|
| CRO69 (Ia-12) | (structure diagram) |

N-(4-(4-morpholino-3-((4-pentylphenyl)sulfonamido)phenyl)thiazol-2-yl)acetamide (Ia-12)

The general procedure for the formation of sulfonamide (I) was followed using 5a-5 (81.0 mg, 0.25 mmol), 4-pentylphenylsulfonyl chloride (76.0 mg, 0.31 mmol) as reagents and triethylamine Purification by silica gel flash chromatography ($CH_2Cl_2$:$CH_3OH$; 100:0 to 94:6) afforded the titled compound as a white powder (75.2 mg, 56%). $^1$H NMR ($CD_3OD$, 200 MHz): δ 0.86 (t, J=6.9 Hz, 3H, $H_{22}$), 1.42-1.14 (m, 4H, $H_{20}$ and $H_{21}$), 1.53 (quint, J=7.3 Hz, 2H, $H_{19}$), 2.22 (s, 3H, $H_1$), 2.45 (dd, J=5.7, 3.4 Hz, 4H, $H_{12}$), 2.60 (t, J=7.6 Hz, 2H, $H_{18}$), 3.78-3.61 (m, 4H, $H_{13}$), 7.16 (d, J=8.3 Hz, 1H, H10), 7.27 (t, J=4.2 Hz, 3H, H4 and H16), 7.60 (dd, J=8.3, 2.1 Hz, 1H, H11), 7.77-7.60 (m, 2H, H15), 8.17 (d, J=2.0 Hz, 1H, H7). 13C NMR (CD3OD, 50 MHz): δ 14.3, 22.6, 23.5, 32.0, 32.4, 36.5, 53.9 (2C), 68.3 (2C), 108.7, 120.1, 123.3, 123.9, 128.2 (2C), 130.2 (2C), 133.7, 134.5, 138.4, 144.4, 150.3, 150.3, 159.5, 170.9. MS-ESI (m/z): [M+H]+=529.2; [M+Na]+=551.3.

| Product ref | Structure |
|---|---|
| CRO24 (IIa-1) | 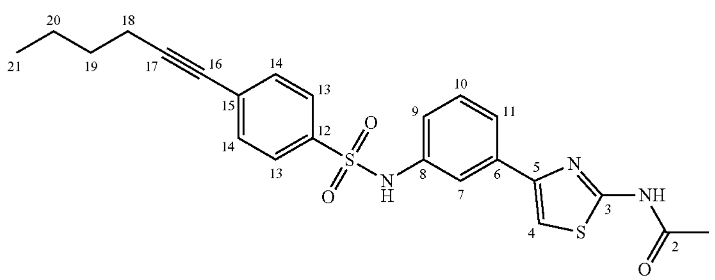 |

N-(4-(3-((4-(hex-1-yn-1-yl)phenyl)sulfonamido)phenyl)thiazol-2-yl)acetamide (IIa-1)

The general procedure for Sonogashira coupling was followed using aryl halide Ia-3 (150.0 mg, 0.33 mmol), Pd(PPh$_3$)$_4$ (57.8 mg, 15% mol.), copper (I) iodide (9.5 mg, 15% mol.) and hex-1-yne (188.0 μL, 1.66 mmol). Purification by silica gel flash chromatography ($CH_2Cl_2$:EtOAc; 100:0 to 70:30) afforded IIa-1 as an off-white powder (117.2 mg, 78%). $^1$H NMR ($CD_3OD$, 200 MHz): δ 0.91 (t, J=7.1 Hz, 3H, $H_{21}$), 1.62-1.35 (m, 4H, $H_{20}$ and $H_{19}$), 2.20 (s, 3H, $H_1$), 2.37 (t, J=6.8 Hz, 2H, $H_{18}$), 6.97 (ddd, J=8.0, 2.2, 0.9 Hz, 1H, $H_9$), 7.27-7.16 (m, 2H, $H_4$ and $H_{10}$), 7.39 (d, J=8.5 Hz, 1H, $H_{14}$), 7.57 (dt, J=7.8, 1.2 Hz, 1H, $H_{11}$), 7.76-7.64 (m, 2H, $H_7$ and $H_{13}$). $^{13}$C NMR ($CD_3OD$, 50 MHz): δ 14.1, 19.8, 22.7, 23.1, 31.9, 80.4, 95.4, 109.3, 120.2, 121.8, 123.6, 128.4 (2C), 130.4, 130.5, 132.9 (2C), 137.2, 139.3, 139.7, 150.5, 159.6, 171.0. HRMS-ESI (m/z): [M+H]$^+$ Calcd for $C_{23}H_{24}N_3O_3S_2$, 454.1254; Found: 454.1249.

| Product name | Structure |
|---|---|
| CRO32 (IIa-2) | 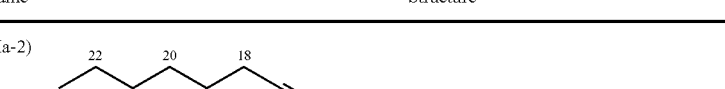 |

N-(4-(3-((4-(oct-1-yn-1-yl)phenyl)sulfonamido)phenyl)thiazol-2-yl)acetamide (IIa-2)

The general procedure for the Sonogashira coupling was followed using aryl halide Ia-3 (400.0 mg, 0.88 mmol), Pd(Ph$_3$)$_4$ (152.5 mg, 15% mol.), copper (I) iodide (25.1 mg, 15% mol.) and oct-1-yne (653.2 µL, 4.43 mmol). Purification by silica gel flash chromatography (CH$_2$Cl$_2$:EtOAc; 100:0 to 70:30) afforded IIa-2 as an off-white powder (330.1 mg, 78%). $^1$H NMR (CD$_3$OD, 200 MHz): δ 0.97-0.78 (m, 3H, H$_{23}$), 1.62-1.15 (m, 9H, H$_{22}$, H$_{21}$, H$_{20}$ and H$_{19}$), 2.19 (s, 3H, H$_1$), 2.34 (t, J=6.8 Hz, 2H, H$_{18}$), 6.97 (ddd, J=8.0, 2.1 and 0.9 Hz, 1H, H$_9$), 7.26-7.14 (m, 2H, H$_4$ and H$_{10}$), 7.38 (d, J=8.5 Hz, 2H, H$_{14}$), 7.56 (d, J=7.9 Hz, 1H, H$_{11}$), 7.74-7.65 (m, 3H, H$_7$ and H$_{13}$). $^{13}$C NMR (CD$_3$OD, 50 MHz): δ 14.5, 20.2, 22.7, 23.7, 29.7, 29.8, 32.6, 80.4, 95.4, 109.3, 120.1, 121.7, 123.6, 128.4 (2C), 130.3, 130.5, 132.9 (2C), 137.1, 139.3, 139.7, 150.4, 159.6, 171.0. HRMS-ESI (m/z): [M+H]$^+$ Calcd for C$_{25}$H$_{28}$N$_3$O$_3$S$_2$, 482.1567; Found: 482.1565.

| Product name | Structure |
|---|---|
| AM305 (IIa-3) | 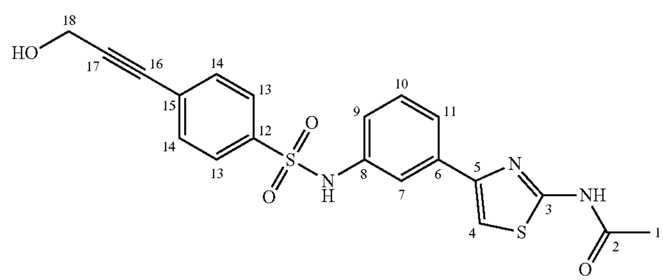 [SMILES: CC(=O)Nc1nc(-c2cccc(NS(=O)(=O)c3ccc(C#CCO)cc3)c2)cs1] |

N-(4-(3-((4-(3-hydroxyprop-1-yn-1-yl)phenyl)sulfonamido)phenyl)thiazol-2-yl)acetamide (IIa-3)

The general procedure for the Sonogashira coupling was followed using Ia-4 (300.0 mg, 0.66 mmol), Pd(PPh$_3$)$_4$ (114.4 mg, 15% mol.), copper (I) iodide (18.9 mg, 15% mol.) and propargyl alcohol (190.4 µL, 3.30 mmol). Purification by silica gel flash chromatography (CH$_2$Cl$_2$:CH$_3$OH; 100:0 to 95:5) afforded IIa-3 as a white-yellowish powder (201.9 mg, 72%). $^1$H NMR (CD$_3$OD, 200 MHz): δ 2.20 (s, 1H, H$_1$), 4.36 (s, 2H, H$_{18}$), 6.97 (ddd, J=8.0, 2.2, 1.0 Hz, 1H, H$_9$), 7.34-7.14 (m, 2H, H$_4$ and H$_{10}$), 7.51-7.42 (m, 2H, H$_{14}$), 7.63-7.53 (m, 1H, H$_{11}$), 7.78-7.66 (m, 3H, H$_7$ and H$_{13}$). $^{13}$C NMR (CD$_3$OD, 50 MHz): δ 22.7, 51.2, 84.0, 92.7, 109.3, 120.2, 121.8, 123.7, 128.5 (2C), 129.1, 130.6, 133.1 (2C), 137.2, 139.3, 140.6, 150.5, 159.6, 171.1. HRMS-ESI (m/z): [M+H]$^+$ Calcd for C$_{20}$H$_{18}$N$_3$O$_4$S$_2$, 428.0733; Found: 428.0736.

| Product ref | Structure |
|---|---|
| AM311 (IIa-4) | 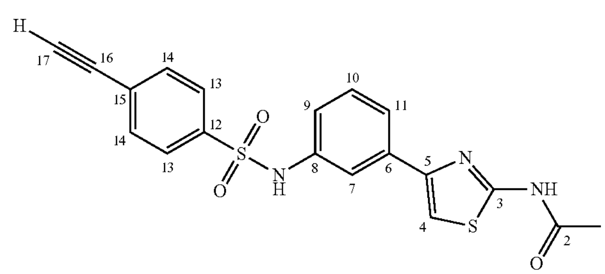 |

N-(4-(3-((4-ethynylphenyl)sulfonamido)phenyl)thiazol-2-yl)acetamide (IIa-4)

The general procedure for Sonogashira coupling was followed using Ia-4 (300.0 mg, 0.66 mmol), PdP(Ph$_3$)$_4$ (114.4 mg, 15% mol.), copper (I) iodide (18.9 mg, 15% mol.) and trimethylsilylacetylene (281.9 μL, 1.98 mmol). After completion of the reaction (about 2 h), the mixture was filtered through a pad of silica (eluted with CH$_2$Cl$_2$/EtOAc 70:30) and the filtrate was concentrated under reduced pressure. The black residue was dissolved in CH$_2$Cl$_2$/CH$_3$OH (1:1; 2 mL:2 mL) and K$_2$CO$_3$ (456.1 mg, 3.3 mmol) was added to the mixture. The resulting suspension was stirred at r.t. for 5 h., adsorbed onto silica prior to purification by silica gel flash chromatography (CH$_2$Cl$_2$/CH$_3$OH; 100:0 to 95:0) to afford the pure titled compound as a yellow-brownish powder (88.2 mg, 34%). $^1$H NMR (CD$_3$OD, 200 MHz): δ 2.20 (s, 3H, H$_1$), 3.70 (s, 1H, H$_{17}$), 6.97 (ddd, J=7.9, 2.3, 1.1 Hz, 1H, H$_9$), 7.30-7.14 (m, 2H, H$_{10}$ and H$_4$), 7.62-7.44 (m, 3H, H$_{11}$ and H$_{14}$), 7.80-7.67 (m, 3H, H$_7$ and H$_{13}$). $^{13}$C NMR (CD$_3$OD, 50 MHz): δ 22.7, 82.4, 82.9, 109.4, 120.2, 121.8, 123.7, 128.4 (3C), 130.6, 133.6 (2C), 137.2, 139.2, 141.0, 150.4, 159.6, 171.0. HRMS-ESI (m/z): [M+H]$^+$ Calcd for C$_{19}$H$_{16}$N$_3$O$_3$S$_2$, 398.0628; Found: 298.0626.

| Product ref | Structure |
|---|---|
| AM366 (IIa-5) | 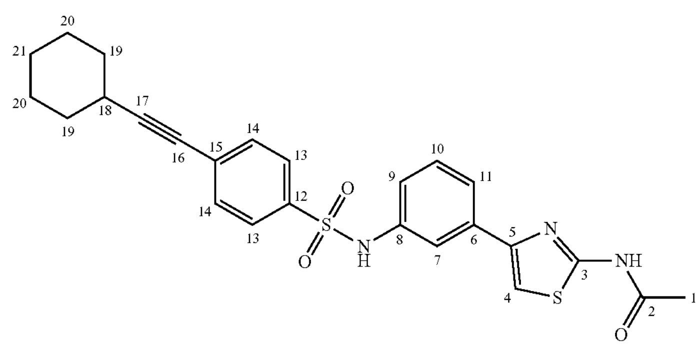 [SMILES: CC(=O)Nc1nc(-c2cccc(NS(=O)(=O)c3ccc(C#CC4CCCCC4)cc3)c2)cs1] |

N-(4-(3-((4-(cyclohexylethynyl)phenyl)sulfonamido)phenyl)thiazol-2-yl)acetamide (IIa-5)

The general procedure for Sonogashira coupling was followed using Ia-4 (110 mg, 0.24 mmol), Pd(Ph$_3$)$_2$Cl$_2$ (25.7 mg, 15% mol.), copper (I) iodide (7.0 mg, 15% mol.) and cyclohexylacetylene (159.4 μL, 1.22 mmol). Purification by silica gel flash chromatography (cyclohexane:EtOAc; 100:0 to 70:30) afforded IIa-5 as a white-yellowish powder (55 mg, 47%). $^1$H NMR (Acetone-d$_6$, 200 MHz): δ 1.58-1.22 (m, 6H, H$_{20}$ and H$_{21}$), 1.91-1.61 (m, 4H, H$_{19}$), 2.28 (s, 3H, H$_1$), 2.70-2.49 (m, 1H, H$_{18}$), 7.09 (ddd, J=8.0, 2.3, 1.1 Hz, 1H, H$_9$), 7.26 (t, J=7.9 Hz, 1H, H$_{10}$), 7.38 (s, 1H, H$_4$), 7.48 (d, J=8.4 Hz, 2H, H$_{14}$), 7.61 (d, J=7.7 Hz, 1H, H$_{11}$), 7.75 (d, J=8.5 Hz, 2H, H$_{13}$), 7.85 (t, J=1.9 Hz, 1H, H$_7$), 9.10 (s, 1H, NH$_{sulfonamide}$), 11.17 (s, 1H, NH$_{acetyl}$). $^{13}$C NMR (Acetone-d$_6$, 50 MHz): δ 22.9, 25.4 (2C), 26.5, 30.3, 33.2 (2C), 80.3, 99.0, 108.8, 119.6, 121.2, 123.1, 128.2 (2C), 129.7, 130.3, 132.7 (2C), 136.8, 139.0, 139.6, 149.7, 159.0, 169.2. HRMS-ESI (m/z): [M+H]$^+$ Calcd for C$_{25}$H$_{26}$N$_3$O$_3$S$_2$, 480.1410; Found: 480.1413.

| Product ref | Structure |
|---|---|
| CRO54 (IIa-6) | *(structure: 4-(oct-1-yn-1-yl)phenyl sulfonamide linked to 3-(2-aminothiazol-4-yl)phenyl, with numbered atoms 1–21)* |

N-(3-(2-aminothiazol-4-yl)phenyl)-4-(oct-1-yn-1-yl)benzenesulfonamide (IIa-6)

A suspension of IIa-2 in 2M aq. HCl/EtOH (1 mL/1 mL) was stirred 2 h at 80° C., then 15 h at 50° C. The mixture was partitioned between EtOAc and saturated aq. $Na_2CO_3$, the aqueous phase was extracted with EtOAc once. The combined organic layers were dried with $Na_2SO_4$ and concentrated under reduced pressure to afford the pure titled compound as a pale yellow solid (20.8 mg, 99%). $R_f$(EtOAc/cyclohexane, 1/1, v/v)=0.65. $^1$H NMR ($CD_3OD$, 200 MHz): δ 1.00-0.77 (m, 3H, $H_{21}$), 1.73-1.18 (m, 8H, $H_{17}$, $H_{18}$, $H_{19}$ and $H_{20}$), 2.39 (t, J=6.8 Hz, 2H, $H_{16}$), 6.73 (s, 1H, $H_2$), 7.08-6.92 (m, 1H, $H_8$), 7.20 (t, J=8.1 Hz, 1H, $H_8$), 7.51-7.35 (m, 4H, $H_{aro}$), 7.76-7.62 (m, 2H, $H_{aro}$). $^{13}$C NMR ($CD_3OD$, 50 MHz): δ 14.4, 20.0, 23.6, 29.6, 29.7, 32.5, 90.3, 95.2, 103.5, 120.0, 121.4, 123.5, 128.2 (2C), 130.2, 130.3, 132.8 (2C), 137.2, 139.1, 139.6, 150.9, 171.3. HRMS-ESI (m/z): $[M+H]^+$ Calcd for $C_{23}H_{26}N_3O_2S_2$, 440.1461; Found: 440.1472.

| Product ref | Structure |
|---|---|
| AM362 (IIa-7) | *(structure: 4-(oct-1-yn-1-yl)phenyl sulfonamide linked to 3-(2-(methylamino)thiazol-4-yl)phenyl, with numbered atoms 1–22)* |

N-(3-(2-(methylamino)thiazol-4-yl)phenyl)-4-(oct-1-yn-1-yl)benzenesulfonamide (IIa-7)

The general procedure for Sonogashira coupling was followed using Ia-9 (325.0 mg, 0.77 mmol), $Pd(PPh_3)_2Cl_2$ (80.6 mg, 15% mol.), copper (I) iodide (21.9 mg, 15% mol.) and oct-1-yne (565.0 μL, 3.83 mmol). Purification by silica gel flash chromatography (cyclohexane:EtOAc; 100:0 to 70:30) afforded IIa-7 as an off-white powder (80 mg, 23%). $^1$H NMR (Acetone-$d_6$, 200 MHz): δ 0.85 (t, J=6.4 Hz, 3H, $H_{22}$), 1.70-1.18 (m, 8H, $H_{18}$, $H_{19}$, $H_{20}$ and $H_{21}$), 2.40 (t, J=6.8 Hz, 2H, $H_{17}$), 3.12-2.88 (m, 3H, $H_1$), 6.73 (s, 1H, $NH_{thiazole}$), 6.87 (s, 1H, $H_3$), 7.11 (ddd, J=8.0, 2.2, 1.2 Hz, 1H, $H_8$), 7.23 (t, J=7.8 Hz, 1H, $H_9$), 7.53-7.44 (m, 2H, $H_{13}$), 7.58 (dt, J=7.7, 1.4 Hz, 1H, $H_{10}$), 7.91-7.70 (m, 3H, $H_6$ and $H_{12}$), 9.10 (s, 1H, $NH_{sulfonamide}$). $^{13}$C NMR (Acetone-$d_6$, 50 MHz): δ 14.4, 19.8, 23.2, 29.2, 29.3, 31.8, 32.1, 80.2, 95.2, 102.0, 119.5, 120.6, 123.0, 128.2 (2C), 129.6, 130.0, 132.7 (2C), 137.4, 138.8, 139.7, 151.4, 170.7. HRMS-ESI (m/z): $[M+H]^+$ Calcd for $C_{24}H_{28}N_3O_2S_2$, 454.1618; Found: 454.1615.

| Product | Structure |
|---|---|
| AM369 (IIa-8) | 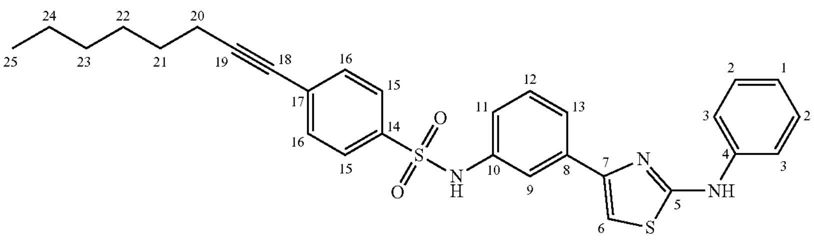 [SMILES: CCCCCCC#Cc1ccc(S(=O)(=O)Nc2cccc(-c3csc(Nc4ccccc4)n3)c2)cc1] |

4-(oct-1-yn-1-yl)-N-(3-(2-(phenylamino)thiazol-4-yl)phenyl)benzenesulfonamide (IIa-8)

The general procedure for Sonogashira coupling was followed using Ia-10 (100.0 mg, 0.21 mmol), Pd(PPh$_3$)$_2$Cl$_2$ (21.6 mg, 15% mol.), copper (I) iodide (5.9 mg, 15% mol.) and oct-1-yne (151.7 μL, 1.03 mmol). Purification by silica gel flash chromatography (cyclohexane:EtOAc; 100:0 to 70:30) afforded IIa-8 as a brown powder (82 mg, 75%). $^1$H NMR (Acetone-d$_6$, 200 MHz): δ 0.86 (t, J=6.2 Hz, 3H, H$_{25}$), 1.67-1.11 (m, 8H, H$_{21}$, H$_{22}$, H$_{23}$ and H$_{24}$), 2.39 (t, J=6.7 Hz, 2H, H$_{20}$), 7.01 (t, J=7.3 Hz, 1H, H$_{12}$), 7.13 (d, J=9.1 Hz, 2H, H$_6$ and H$_{11}$), 7.33 (dt, J=15.6, 7.8 Hz, 3H, H$_1$ and H$_3$), 7.48 (d, J=8.2 Hz, 2H, H$_{16}$), 7.66 (d, J=7.7 Hz, 1H, H$_{13}$), 7.88-7.73 (m, 4H, H$_2$ and H$_{15}$), 7.92 (t, J=1.9 Hz, 1H, H$_9$), 9.14 (s, 1H, NH$_{thiazole}$), 9.35 (s, 1H, NH$_{sulfonamide}$). $^{13}$C NMR (Acetone-d$_6$, 50 MHz): δ 14.4, 19.8, 23.2, 29.2, 29.3, 32.1, 80.2, 95.3, 103.8, 118.3 (2C), 119.5, 120.8, 122.6, 123.0, 128.2 (2C), 129.7, 129.9 (2C), 130.3, 132.7 (2C), 137.0, 139.0, 139.7, 142.4, 151.3, 164.5. HRMS-ESI (m/z): [M+H]$^+$ Calcd for C$_{29}$H$_{30}$N$_3$O$_2$S$_2$, 516.1774; Found: 516.1777.

| Product ref | Structure |
|---|---|
| CRO47 (IIa-9) | 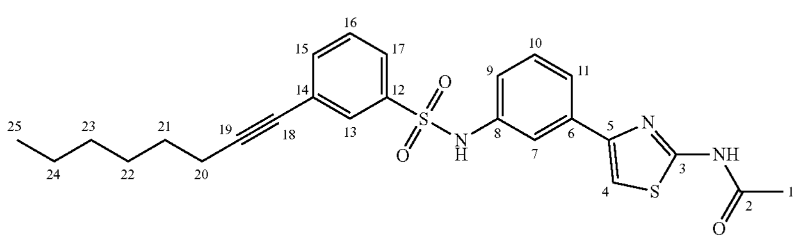 [SMILES: CCCCCCC#Cc1cccc(S(=O)(=O)Nc2cccc(-c3csc(NC(C)=O)n3)c2)c1] |

N-(4-(3-((3-(oct-1-yn-1-yl)phenyl)sulfonamido)phenyl)thiazol-2-yl)acetamide (IIa-9)

The general procedure for Sonogashira coupling was followed using Ia-8 (113.0 mg, 0.25 mmol), Pd(PPh$_3$)$_4$ (44.0 mg, 15% mol.), copper (I) iodide (5.0 mg, 10% mol.) and oct-1-yne (185.0 μL, 1.25 mmol). Purification by silica gel flash chromatography (cyclohexane:EtOAc; 100:0 to 60:40) afforded IIa-9 as a white-yellowish powder (103.0 mg, 86%). R$_f$ (EtOAc/cyclohexane, 1/1, v/v)=0.57. $^1$H NMR (CD$_3$Cl, 200 MHz): δ 0.86 (t, J=6.0 Hz, 3H, H$_{25}$), 1.41-1.20 (m, 6H, H$_{22}$, H$_{23}$ and H$_{24}$), 1.63-1.45 (m, 2H, H$_{21}$), 2.04 (s, 1H, H$_1$), 2.33 (t, J=6.9 Hz, 2H, H$_{20}$), 7.00-6.85 (m, 2H, H$_{aro}$), 7.12 (t, J=8.0 Hz, 1H, H$_{10}$), 7.34-7.21 (m, 2H, H$_{aro}$), 7.50-7.39 (m, 3H, H$_{aro}$), 7.61 (d, J=7.9 Hz, 2H, H$_{aro}$), 7.83 (s, 1H, H$_{aro}$), 10.51 (s, 1H, NH$_{sulfonamide}$). $^{13}$C NMR (CD$_3$Cl, 50 MHz): δ 14.3, 19.6, 22.7, 23.2, 28.7, 28.8, 31.5, 79.1, 93.6, 108.9, 120.3, 121.7, 123.5, 125.8, 126.0, 129.2, 129.9, 130.3, 135.7, 136.1, 136.9, 139.5, 148.7, 159.0, 168.6. HRMS-ESI (m/z): [M+H]$^+$ Calcd for C$_{25}$H$_{28}$N$_3$O$_3$S$_2$, 482.1567; Found: 482.1574.

| Product ref | Structure |
|---|---|
| CRO49 (IIa-10) | (structure) |

N-(4-(3-((3-(3-hydroxyprop-1-yn-1-yl)phenyl)sulfo-namido)phenyl)thiazol-2-yl)acetamide (IIa-10)

The general procedure for Sonogashira coupling was followed using Ia-8 (113.0 mg, 0.25 mmol), Pd(PPh$_3$)$_4$ (44.0 mg, 15% mol.), copper (I) iodide (5.0 mg, 10% mol.) and propargyl alcohol (72.0 μL, 1.25 mmol). Purification by silica gel flash chromatography (cyclohexane:EtOAc; 100:0 to 60:40) afforded IIa-10 as a white powder (76.1 mg, 71%), along with unreacted starting material X (22.0 mg, 20%). R$_f$ (EtOAc/cyclohexane, 2/1, v/v)=0.38. $^1$H NMR (CD$_3$OD, 200 MHz): δ 2.21 (s, 3H, H$_1$), 4.37 (s, 2H, H$_{20}$), 6.99 (ddd, J=8.1, 2.3, 1.1 Hz, 1H, H$_9$), 7.29-7.17 (m, 2H, H$_4$ and H$_{10}$), 7.41 (t, J=7.8 Hz, 1H, H$_{16}$), 7.62-7.51 (m, 2H, H$_{aro}$), 7.71 (tt, J=3.4, 1.5 Hz, 2H, H$_{aro}$), 7.80 (t, J=1.8 Hz, 1H, H$_{aro}$). $^{13}$C NMR (CD$_3$OD, 50 MHz): δ 22.7, 51.2, 83.7, 91.2, 109.3, 120.1, 121.7, 123.7, 125.5, 128.0, 130.4, 130.6, 131.0, 136.7, 137.2, 139.2, 141.6, 150.4, 159.6, 171.1. HRMS-ESI (m/z): [M+H]$^+$ Calcd for C$_{20}$H$_{18}$N$_3$O$_4$S$_2$, 428.0733; Found: 428.0737.

| Product ref | Structure |
|---|---|
| CRO50 (IIa-11) | (structure) |

N-(4-(3-((3-((trimethylsilyl)ethynyl)phenyl)sulfona-mido)phenyl)thiazol-2-yl)acetamide (IIa-11)

The general procedure for Sonogashira coupling was followed using Ia-8 (113.0 mg, 0.25 mmol), Pd(PPh$_3$)$_4$ (44.0 mg, 15% mol.), copper (I) iodide (5.0 mg, 10% mol.) and trimethylsilylacetylene (178.0 μL, 1.25 mmol). Purification by silica gel flash chromatography (cyclohexane:EtOAc; 100:0 to 50:50) afforded IIa-11 as a pale yellow powder (98.2 mg, 84%). R$_f$(EtOAc/cyclohexane, 1/1, v/v)=0.52. $^1$H NMR (CD$_3$Cl, 200 MHz): δ 0.17 (s, 9H, H$_{20}$), 1.94 (s, 3H, H$_1$), 6.89 (d, J=7.1 Hz, 2H, H$_{aro}$), 7.08 (t, J=7.8 Hz, 1H, H$_{aro}$), 7.46-7.17 (m, 3H, H$_{aro}$), 7.53 (d, J=7.5 Hz, 1H, H$_{aro}$), 7.66 (d, J=8.0 Hz, 1H, H$_{aro}$), 7.90 (s, 1H, H$_{aro}$), 8.18 (s, 1H, NH$_{sulfonamide}$), 10.97 (s, 1H, NH$_{acetyl}$). $^{13}$C NMR (CD$_3$Cl, 50 MHz): δ 0.1 (3C), 23.0, 97.5, 102.9, 109.0, 120.0, 121.5, 123.4, 124.7, 126.9, 129.3, 129.9, 130.6, 135.6, 136.4, 136.9, 139.6, 148.6, 159.4, 169.0. HRMS-ESI (m/z): [M+H]$^+$ Calcd for C$_{22}$H$_{24}$N$_3$O$_3$S$_2$Si, 470.1023; Found: 470.1033.

| Product ref | Structure |
|---|---|
| CRO53 (IIa-12) | 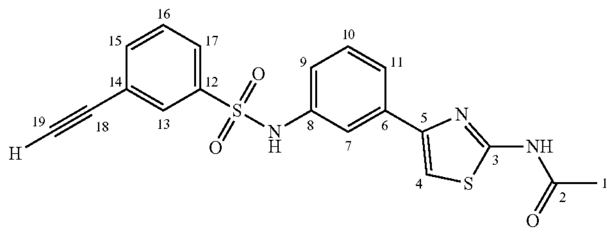 [SMILES: C#Cc1cccc(S(=O)(=O)Nc2cccc(-c3csc(NC(C)=O)n3)c2)c1] |

N-(4-(3-((3-ethynylphenyl)sulfonamido)phenyl)thiazol-2-yl)acetamide (IIa-12)

To a yellow solution of Ia-8 (51 mg, 0.108 mmol) in methanol (4 mL) was added solid $K_2CO_3$ (138 mg, 1.0 mmol). The resulting suspension was stirred at r.t. for 14 h. The mixture was partitioned between EtOAc and water, the aqueous phase was extracted with EtOAc once. The combined organic layers were washed with brine, dried with $Na_2SO_4$ and concentrated under reduced pressure. Purification by silica gel flash chromatography (cyclohexane: EtOAc; 100:0 to 50:50) afforded IIa-12 as a white powder (41.8 mg, 97%). $R_f$(EtOAc/cyclohexane, 1/1, v/v)=0.47. $^1$H NMR (CD$_3$OD, 200 MHz): δ 2.21 (s, 3H, H$_1$), 3.64 (s, 1H, H$_{alkyne}$), 6.99 (ddd, J=8.1, 2.3, 1.1 Hz, 1H, H$_9$), 7.33-7.16 (m, 2H, H$_4$ and H$_{10}$), 7.42 (t, J=7.8 Hz, 1H, H$_{16}$), 7.59 (ddt, J=7.8, 3.5, 1.4 Hz, 2H, H$_{aro}$), 7.73 (dt, J=6.5, 1.6 Hz, 2H, H$_{aro}$), 7.85 (t, J=1.7 Hz, 1H, H$_{aro}$). $^{13}$C NMR (CD$_3$OD, 50 MHz): δ 22.7, 81.1, 82.7, 109.3, 120.2, 121.7, 123.7, 124.9, 128.4, 130.4, 130.6, 131.5, 137.2, 137.2, 139.2, 141.6, 150.4, 159.6, 171.1. HRMS-ESI (m/z): [M+H]$^+$ Calcd for $C_{19}H_{16}N_3O_3S_2$, 398.0628; Found: 398.0626.

| Product ref | Structure |
|---|---|
| AM302 (IIIa-1) | 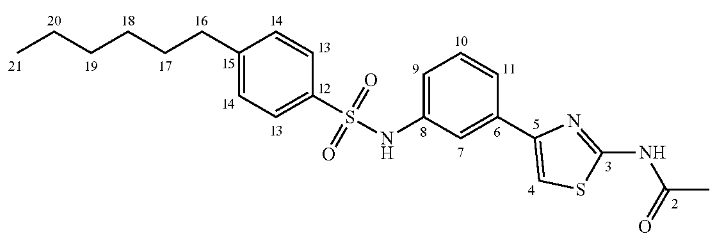 |

N-(4-(3-((4-hexylphenyl)sulfonamido)phenyl)thiazol-2-yl)acetamide (IIIa-1)

The reduction of IIa-1 was completed using a continuous flow apparatus. IIa-1 (100.0 mg, 0.22 mmol) was dissolved in CH$_3$OH (HPLC grade, 8 mL) and passed through a Pd/C (10%) cartridge at a flow of 0.5 mL·min$^{-1}$, at 40° C. under 1 bar of H$_2$. The solvent was removed under reduced pressure to afford the pure titled compound as a white powder (87.3 mg, 87%). $^1$H NMR (CD$_3$OD, 200 MHz): δ 0.86-0.80 (m, 3H, H$_{21}$), 1.30-1.13 (m, 6H, H$_{18}$, H$_{19}$ and H$_{20}$), 1.60-1.43 (m, 2H, H$_{17}$), 2.20 (s, 3H, H$_1$), 2.57 (t, J=7.6 Hz, 2H, H$_{16}$), 6.99 (ddd, J=7.9, 2.3, 1.1 Hz, 1H, H$_9$), 7.30-7.12 (m, 4H, H$_4$, H$_{10}$ and H$_{14}$), 7.69-7.53 (m, 4H, H$_7$, H$_{11}$ and H$_{13}$). $^{13}$C NMR (CD$_3$OD, 50 MHz): δ 14.4, 22.6, 23.6, 29.9, 32.1, 32.7, 36.6, 109.0, 119.9, 121.6, 123.3, 128.3 (2C), 130.0 (2C), 130.3, 136.9, 138.1, 139.4, 149.8, 150.4, 159.4, 170.9. HRMS-ESI (m/z): [M+H]$^+$ Calcd for $C_{23}H_{28}N_3O_3S_2$, 458.1572; Found: 458.1570.

| Product ref | Structure |
|---|---|
| AM309 (IIIa-2) | (structure diagram) |

(Z)—N-(4-(3-((4-(oct-1-en-1-yl)phenyl)sulfonamido)phenyl)thiazol-2-yl)acetamide (IIIa-2)

To a solution of IIa-2 (114.0 mg, 0.24 mmol) in CH$_3$OH (technical grade, 20 mL) was added Lindlar palladium (29.0 mg, 20% wt). The reaction mixture was allowed to react 2 h at r.t. and was filtered through a pad of Celite®. The resulting filtrate was concentrated under reduced pressure to afforded pure IIIa-2 as a white powder (86.7 mg, 74%). $^1$H NMR (CD$_3$OD, 200 MHz): δ 0.83 (t, J=6.2 Hz, 3H, H$_{23}$), 1.44-1.12 (m, 8H, H$_{19}$, H$_{20}$, H$_{21}$ and H$_{22}$), 2.20 (s, 5H, H$_1$ and H$_{18}$) 5.74 (dt, J=11.8, 7.4 Hz, 1H, H$_{17}$), 6.37 (d, J=11.6 Hz, 1H, H$_{18}$), 7.09-6.90 (m, 1H, H$_9$), 7.42-7.13 (m, 4H, H$_{10}$, H$_4$ and H$_{14}$), 7.57 (d, J=7.8 Hz, 1H, H$_{11}$), 7.78-7.62 (m, 3H, H$_7$ and H$_{13}$). $^{13}$C NMR (CD$_3$OD, 50 MHz): δ 14.5, 22.7, 23.8, 29.7, 30.1, 30.8, 32.9, 109.2, 120.1, 121.8, 123.5, 128.3 (2C), 128.6, 130.2 (2C), 130.5, 137.0, 137.1, 138.7, 139.5, 143.9, 150.5, 159.6, 171.0. HRMS-ESI (m/z): [M+H]$^+$ Calcd for C$_{25}$H$_{30}$N$_3$O$_3$S$_2$, 484.1723; Found: 484.1729.

| Product ref | Structure |
|---|---|
| AM295 (IIIa-3) | (structure diagram) |

N-(4-(3-((4-octylphenyl)sulfonamido)phenyl)thiazol-2-yl)acetamide (IIIa-3)

The reduction of IIa-2 was completed using a continuous flow apparatus. IIa-2 (60.0 mg, 0.16 mmol) was dissolved in CH$_3$OH (HPLC grade, 5 mL) and passed through a Pd/C (10%) cartridge at a flow of 0.5 mL·min$^{-1}$, at 40° C. under 1 bar of H$_2$. The solvent was removed under reduced pressure to afford the pure titled compound as a white powder (35.2 mg, 60%). $^1$H NMR (CD$_3$OD, 200 MHz): δ 0.85 (t, J=6.5 Hz, 3H, H$_{23}$), 1.23 (d, J=11.3 Hz, 10H, H$_{22}$, H$_{21}$, H$_{20}$, H$_{29}$ and H$_{18}$), 1.53-1.43 (m, 2H, H$_{17}$), 2.20 (s, 3H, H$_1$), 2.55 (t, J=8.0 Hz, 2H, H$_{16}$), 6.99 (dd, J=7.5, 1.6 Hz, 1H, H$_9$), 7.30-7.10 (m, 4H, H$_4$, H$_{10}$ and H$_{14}$), 7.60-7.49 (m, 1H, H$_{11}$), 7.74-7.60 (m, 3H, H$_7$ and H$_{13}$). $^{13}$C NMR (CD$_3$OD, 50 MHz): δ 14.6, 22.7, 23.8, 30.3, 30.5, 30.6, 32.3, 33.1, 36.8, 109.2, 120.0, 121.7, 123.4, 128.4 (2C), 130.1 (2C), 130.4, 137.0, 138.3, 139.6, 149.9, 150.5, 159.5, 171.0. HRMS-ESI (m/z): [M+H]$^+$ Calcd for C$_{25}$H$_{32}$N$_3$O$_3$S$_2$, 486.1884; Found: 486.1880.

Example 8: Anti-Cancer Activities of Compounds of the Invention

Material & Methods
Experimental Protocol for Assessment of Potency and Efficacy
Cell Cultures Normal human melanocytes (NHM) prepared from foreskins of newborns were grown under 5% CO$_2$ at 37° C. in MCDB 153 (Sigma) supplemented with 2% FCS, bovine pituitary extract (10 μg/ml), PMA (8 nM), bFGF (1 ng/ml), insulin (5 μg/ml), hydrocortisone (0.5 μg/ml), forskolin (10 μM), gentamicin (20 μg/ml), penicillin/streptomycin/amphotericin B (100 U/ml) (Invitrogen).

Normal human fibroblasts prepared from foreskins of newborns were grown under 5% CO$_2$ at 37° C. in DMEM medium supplemented with 10% FCS and penicillin/streptomycin (100 U/ml/50 mg/ml).

Different melanoma cell lines were purchased from American Tissue Culture Collection (Molsheim, France). Cells were grown in RPMI 1640 (A375, WM9 and patient melanoma cells) or in DMEM medium (Mel501) supplemented with 10% FCS and penicillin/streptomycin (100 U/ml/50 mg/ml) at 37° C. and 5% CO$_2$.

Patient melanoma cells were prepared from biopsy after digestion for 1-2 h with collagenase A (0.33 U/ml), dispase (0.85 U/ml) and Dnase I (144 U/ml) at 37° C. Large debris were removed by filtration through a 70-mm cell strainer.
Trypan Blue Assays Cells were seeded in 6-well plates (60000 cells/well), depleted and incubated with compounds for the times indicated. Then cells were detached in the presence of 200 μl of HyQTase (Thermo) and 2 ml of RPMI 1640 Glutamax (Gibco) was added to the cell solution. 10 µl of this solution was stained for 1 minute with 10µl of 0.4% trypan blue before counting with a Malassez chamber.

Western Blot Assays

Proteins were extracted in Fisher buffer containing TRIS-HCl pH 7.5 50 mM, NaCl 15 mM, Triton X-100 1% and proteases and phosphatases inhibitors. Briefly, cell lysates (30 µg) were separated by SDS-PAGE, transferred onto a PVDF membrane (Millipore, Molsheim, France) and then exposed to the appropriate antibodies. Proteins were visualized with the ECL system from Amersham (Arlington, Heights, Ill., USA). The western blots shown are representative of at least 3 independent experiments.

RESULTS

FIG. 1: The Effect of Compounds Ia-7, IIIa-3, IIIa-1, IIIa-2, IIa-2, IIa-9, Ia-4, IIa-11, IIa-12, IIa-6, Compared to Ia-1, on Cell Viability on A375 Melanoma Cells.

Cell viability was assessed by measuring the number of cells alive in samples of different cells. The measure of cell viability as performed by cell counting using the trypan blue exclusion method. Results were expressed as the percentage of cells alive relatively to the number of living cells in the presence of DMSO, which corresponds to the negative control associated to the 100% value.

As depicted in FIG. 1, all new compounds displayed a better activity on A375 melanoma cells than the reference compound Ia-1 having a nude phenyl group. This clearly showed the benefit of introducing apolar substituents on this ring. A clear correlation between the size of the apolar group and the activity could be drawn and demonstrated having a greater impact on the viability than the substitution position (para versus meta). The very active compounds IIa-2, IIIa-1 and IIIa-3 substituted in para position respectively with an octyne, hexyl and octyl chain, were selected to investigate their potential to promote cell death on resistant melanoma cell lines as well as other cancer cell lines.

FIG. 2a. Effect of Compounds IIa-2, IIIa-1 and IIIa-3 on Cell Viability on Melanoma Cells. PLX4032 was Used as a Positive Control.

FIG. 2A shows a strong activity of compounds IIa-2, IIIa-1 and IIIa-3 at 10 µM on both sensitive and resistant melanoma cell lines, contrary to reference B-Raf inhibitor drug PLX4032 which looses most activity on resistant A375 R5C3 an A375 RIV cell lines.

FIG. 2b. Effect of Compounds IIa-2, IIIa-1 and IIIa-3 on Cell Viability on CML Cells. Imatinib was Used as a Positive Control.

The activity of compounds IIa-2, IIIa-1 and IIIa-3 against CML cells was also evaluated. They showed a viability decrease in the same range than the standard BCR-ABL inhibitor Imatinib on sensitive K562 CML cells, and proved much more active on resistant K562 cells, displaying almost total mortality for IIa-2 at this concentration.

FIG. 2c. Effect of Compounds IIa-2, IIIa-1 and IIIa-3 on Cell Viability on Pancreatic Cancer Cells. Gemcitabine was Used as a Positive Control.

The compounds IIa-2, IIIa-1 and IIIa-3 were next evaluated against pancreatic cells, BxPC3 (sensitive) and MiaPACA cell lines (resistant to the nucleoside analog Gemcitabine). All 3 compounds demonstrated a very high activity on this cells, in the same range or better than Gemcitabine on sensitive cells. It is worth noting that they were still very active on resistant cells while Gemcitabine proved inactive. The best compound was again IIa-2 which induced total cell death for both cell lines.

FIG. 3: Effect of Compound IIa-2 on the Viability of KHN and FHN Cell Lines.

Primary cell cultures of human normal melanocytes were prepared from human foreskin. In order to determine the effect of compound IIa-2 on cell viability of melanocytes and fibroblasts, different concentration of IIa-2 were added to the cell samples. The measure of cell viability was performed in the same way as for FIG. 1. Results are expressed as the percentage of living cells relatively to the number of living cells in the presence of DMSO, as for FIG. 1.

This figure showed that compound IIa-2 has no effect on normal cells (melanocytes and fibroblasts), which attested for its low toxicity and good pharmacological profile FIG. 4: Western Blots Showing the Mechanism of Death of Compound IIa-2 (Apoptosis Versus Autophagy).

The Western blot in FIG. 4 shows the effect of IIa-2 (CRO32) on PARP (poly(ADP-ribose) polymerase) cleavage (apoptosis) and LCII/LCIII conversion (autophagy). This figure clearly showed that compound IIa-2 (10 µM) induced both apoptosis and autophagy cellular deaths in A375 melanoma cell line. In contrast, only apoptosis is induced by PLX4032, which clearly attest for two different modes of action between IIa-2 and PLX4032. HA15, analogue of IIa-2 featuring a dansyl group, was used as a positive control and showed similar behavior as IIa-2 in this cell line.

REFERENCES

Throughout this application, various references describe the state of the art to which this invention pertains. The disclosures of these references are hereby incorporated by reference into the present disclosure.

The invention claimed is:

1. A compound of general formula (I)

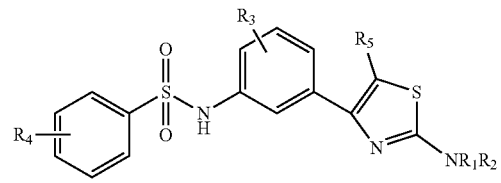

wherein

R$_1$ is selected from H, aryl and alkyl;

R$_2$ is selected from H, alkyl, aryl and CO-R$_6$;

R$_3$ is selected from H, halogen, alkyl, alkenyl, alkynyl, aryl, NHR$_7$, NR$_7$R$_8$, OR$_7$ and SR$_7$;

R$_4$ is (C$_2$-C$_{12}$) alkynyl, wherein the alkynyl group is linear, branched or cyclic and wherein the alkynyl group is optionally substituted with one to three OH groups;

R$_5$ is selected from H, R$_6$, aryl, OH, OR$_6$, O-aryl, SH, SR$_6$, S-aryl, CN, NO$_2$, CF$_3$, COOR$_6$, SO$_2$NR$_7$R$_8$, CONR$_7$R$_8$, NH$_2$, NHR$_6$, NH-aryl, NR$_7$R$_8$, NHCOR$_6$ and aminoacyl;

R$_6$ is alkyl optionally substituted with halogen, OH, SH, NH$_2$, O-alkyl, S-alkyl, NH-alkyl or NH-di(alkyl); and R$_7$ and R$_8$ are identical or different and are H or alkyl optionally substituted with halogen, OH, SH, NH$_2$, O-alkyl, S-alkyl, NH-alkyl or NH-di (alkyl);

and pharmaceutically acceptable salts, tautomers, solvates or isotopic variations thereof;

wherein unless otherwise specified:
Alkyl denotes a straight- or branched hydrocarbon chain comprising 1 to 6 carbon atoms,
Alkenyl denotes a straight- or branched hydrocarbon chain comprising 2 to 6 carbon atoms and one or more double bonds,
Alkynyl denotes a straight- or branched hydrocarbon chain containing 2 to 6 carbon atoms and one or more triple bonds and optionally one or more double bonds, and
Aryl denotes a aromatic carbon ring comprising from 6 to 10 carbon atoms.

2. The compound according to claim 1, wherein $R_1$ is H.
3. The compound according to claim 1, wherein $R_2$ is selected from H, methyl or $COCH_3$.
4. The compound according to claim 1, wherein $R_3$ is H.
5. The compound according to claim 1, wherein $R_4$ is $C\equiv CR_{10}$, wherein $R_{10}$ is selected from H, $C_1$-$C_8$ alkyl, or hydroxy ($C_1$-$C_8$)alkyl.
6. The compound according to claim 1, wherein $R_4$ is in the meta or para position with respect to the sulfonyl group.
7. The compound according to claim 1, wherein the compound is selected from the group consisting of:
N-(4-(3-(4-(oct-1-ynyl)phenylsulfonamido)phenyl)thiazol-2-yl)acetamide
N-(4-(3-(3-(oct-1-ynyl)phenylsulfonamido)phenyl)thiazol-2-yl)acetamide
N-(4-(3-(3-(3-hydroxyprop-1-ynyl)phenylsulfonamido)phenyl)thiazol-2-yl)acetamide
N-(4-(3-(3-ethynylphenylsulfonamido)phenyl)thiazol-2-yl)acetamide
N-(4-(3-((4-(3-hydroxyprop-1-yn-1-yl)phenyl)sulfonamido)phenyl)thiazol-2-yl)acetamide and
N-(4-(3-((4-ethynylphenyl)sulfonamido)phenyl)thiazol-2-yl)acetamide.

8. A method of treating melanoma in a patient in need thereof, comprising administering to the patient a therapeutically effective amount of a
compound of general formula (I)

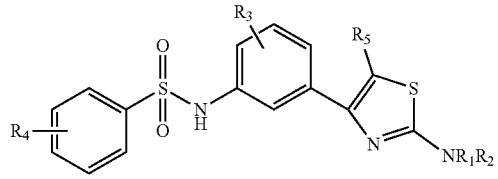

wherein
$R_1$ is selected from H, aryl and alkyl;
$R_2$ is selected from H, alkyl, aryl and CO-$R_6$;
$R_3$ is selected from H, halogen, alkyl, alkenyl, alkynyl, aryl, $NHR_7$, $NR_7R_8$, $OR_7$, $SR_7$;
$R_4$ is ($C_2$-$C_{12}$) alkynyl, wherein the alkynyl group is linear, branched or cyclic;
$R_5$ is selected from H, $R_6$, aryl, OH, $OR_6$, O-aryl, SH, $SR_6$, S-aryl, CN, $NO_2$, $CF_3$, $COOR_6$, $SO_2NR_7R_8$, $CONR_7R_8$, $NH_2$, $NHR_6$, NH-aryl, $NR_7R_8$, $NHCOR_6$ and aminoacyl;
$R_6$ is alkyl optionally substituted with halogen, OH, SH, $NH_2$ O-alkyl, S-alkyl, NH-alkyl or NH-di(alkyl); and
$R_7$ and $R_8$ are identical or different and are alkyl optionally substituted with halogen, OH, SH, $NH_2$ O-alkyl, S-alkyl, NH-alkyl or NH-di (alkyl);
or pharmaceutically acceptable salts, tautomers, solvates or isotopic variations thereof.

9. A pharmaceutical composition comprising a compound of claim 1 and a pharmaceutically acceptable carrier.
10. The method of claim 8, wherein the patient is an animal or human.

* * * * *